(12) United States Patent
Smeltzer et al.

(10) Patent No.: US 11,040,932 B2
(45) Date of Patent: Jun. 22, 2021

(54) SYNTHESIS OF CANNABIGEROL

(71) Applicant: Treehouse Biotech, Inc., Boulder, CO (US)

(72) Inventors: Thomas Smeltzer, Longmont, CO (US); Robert Davis, Boulder, CO (US); Sean Colvin, Gunbarrel, CO (US); Jacob Black, New Haven, CT (US)

(73) Assignee: Treehouse Biotech, Inc., Boulder, CO (US)

( * ) Notice: Subject to any disclaimer, the term of this patent is extended or adjusted under 35 U.S.C. 154(b) by 0 days.

(21) Appl. No.: 16/599,026

(22) Filed: Oct. 10, 2019

(65) Prior Publication Data

US 2020/0115306 A1 Apr. 16, 2020

Related U.S. Application Data

(60) Provisional application No. 62/743,982, filed on Oct. 10, 2018.

(51) Int. Cl.
| | | |
|---|---|---|
| *C07C 39/19* | (2006.01) | |
| *C07C 37/11* | (2006.01) | |
| *C07C 37/68* | (2006.01) | |
| *C07C 43/285* | (2006.01) | |
| *C07F 7/08* | (2006.01) | |
| *B01J 27/128* | (2006.01) | |
| *B01J 31/02* | (2006.01) | |
| *B01J 27/232* | (2006.01) | |
| *B01J 27/08* | (2006.01) | |
| *B01J 27/138* | (2006.01) | |

(52) U.S. Cl.
CPC .............. *C07C 39/19* (2013.01); *B01J 27/08* (2013.01); *B01J 27/128* (2013.01); *B01J 27/138* (2013.01); *B01J 27/232* (2013.01); *B01J 31/0225* (2013.01); *C07C 37/11* (2013.01); *C07C 37/685* (2013.01); *C07C 43/285* (2013.01); *C07F 7/081* (2013.01)

(58) Field of Classification Search
CPC .................... C07C 39/19; C07C 37/11
See application file for complete search history.

(56) References Cited

U.S. PATENT DOCUMENTS

| | | |
|---|---|---|
| 2,304,669 A | 12/1942 | Adams |
| 2,419,934 A | 5/1947 | Adams |
| 3,576,887 A | 4/1971 | Hughes et al. |
| 3,734,930 A | 5/1973 | Razdan et al. |
| 5,137,626 A | 8/1992 | Parry et al. |
| 5,252,490 A | 10/1993 | Elsohly et al. |
| 5,338,753 A | 8/1994 | Burstein et al. |
| 5,633,357 A | 5/1997 | Tius et al. |
| 5,847,128 A | 12/1998 | Martin et al. |
| 6,365,416 B1 | 4/2002 | Elsohly |
| 6,403,126 B1 | 6/2002 | Webster |
| 6,730,519 B2 | 5/2004 | Elsohly |
| 7,700,368 B2 | 4/2010 | Flockhart |
| 8,343,553 B2 | 1/2013 | Hospodor |
| 8,445,034 B1 | 5/2013 | Coles, Jr. |
| 8,497,299 B2 | 7/2013 | Mechoulam et al. |
| 8,673,368 B2 | 3/2014 | Guy |
| 8,771,760 B2 | 7/2014 | Guy et al. |
| 8,846,409 B2 | 9/2014 | Flockhart et al. |
| 8,859,016 B2 | 10/2014 | Pritchett |
| 8,895,078 B2 | 11/2014 | Mueller |
| 8,980,941 B2 | 3/2015 | Hospodor |
| 9,169,455 B2 | 10/2015 | Hamler et al. |
| 9,199,960 B2 | 12/2015 | Ferri |
| 9,376,367 B2 | 6/2016 | Herkenroth et al. |
| 9,526,792 B1 | 12/2016 | Degeeter |
| 9,603,887 B2 | 3/2017 | Kelly |
| 9,655,936 B2 | 5/2017 | Ruben et al. |
| 9,718,065 B1 | 8/2017 | Cilia |
| 9,744,151 B2 | 8/2017 | Gutman et al. |
| 9,808,494 B2 | 11/2017 | Barringer |
| 9,814,775 B2 | 11/2017 | Rossi et al. |
| 9,815,810 B1 | 11/2017 | Ogilvie et al. |
| 9,895,404 B1 | 2/2018 | Baskis |
| 9,901,607 B2 | 2/2018 | Silen |
| 9,913,868 B1 | 3/2018 | Alfiere |
| 9,919,241 B1 | 3/2018 | Auerbach et al. |
| 9,937,147 B2 | 4/2018 | DeGeeter |
| 9,937,218 B2 | 4/2018 | Towle |
| 9,950,275 B1 | 4/2018 | Ruben et al. |
| 9,956,174 B1 | 5/2018 | Nordahl |
| 9,974,820 B2 | 5/2018 | Ablett |
| 9,974,821 B2 | 5/2018 | Kennedy |
| 9,981,203 B2 | 5/2018 | Shuja |
| 10,004,684 B2 | 6/2018 | Whittle et al. |

(Continued)

FOREIGN PATENT DOCUMENTS

| | | |
|---|---|---|
| AU | 2000012348 | 7/2000 |
| AU | 2000012349 | 8/2000 |

(Continued)

OTHER PUBLICATIONS

Lee et al., J. Organic Chemistry, (2002), v.67, p. 8265-8268.*
PCT International Search Report and Written Opinion in International Application PCT/US2019/016182, dated May 27, 2019, 17 pages.
PCT International Search Report and Written Opinion in International Application PCT/US2019/026093, dated Jul. 26, 2019, 10 pages.
Repetto, M., et al., "Separation of cannabinoids", 1976, United Nations Office on Drugs and Crime—Bulletin on Narcotics, issue 4-007, 5 pages (Year: 1976). (with Eng. ab).

(Continued)

*Primary Examiner* — Yong L Chu

(57) ABSTRACT

Multiple methods of synthesizing cannabigerol are presented. Combining olivetol with geraniol derivatives are provided. Cross-coupling methods of combing functionalized resorcinols are provided. Useful intermediates are formed during such cross-coupling steps.

4 Claims, 3 Drawing Sheets

(56) References Cited

U.S. PATENT DOCUMENTS

| | | |
|---|---|---|
| 10,011,804 B2 | 7/2018 | Mancosky |
| 10,016,360 B1 | 7/2018 | Elbogen et al. |
| 10,028,987 B1 | 7/2018 | Pillsbury |
| 10,105,343 B2 | 10/2018 | Kubby |
| 10,137,161 B2 | 11/2018 | Kolsky |
| 10,155,176 B1 | 12/2018 | Feuer et al. |
| 10,179,683 B2 | 1/2019 | Whittle |
| 10,188,628 B1 | 1/2019 | Kershman et al. |
| 10,189,762 B1 | 1/2019 | Oroskar et al. |
| 10,195,159 B2 | 2/2019 | Whittle et al. |
| 10,206,888 B2 | 2/2019 | Vu et al. |
| 10,207,199 B2 | 2/2019 | Nadal Roura |
| 10,213,788 B2 | 2/2019 | Bates |
| 10,214,753 B2 | 2/2019 | Peet et al. |
| 10,226,496 B2 | 3/2019 | Sekura et al. |
| 10,238,705 B2 | 3/2019 | Speier |
| 10,238,706 B1 | 3/2019 | Nahtigal |
| 10,238,745 B2 | 3/2019 | Finley et al. |
| 10,239,808 B1 | 3/2019 | Black et al. |
| 10,245,525 B1 | 4/2019 | Ko |
| 10,246,431 B2 | 4/2019 | Changoer et al. |
| 10,265,295 B2 | 4/2019 | Sorbo et al. |
| 2003/0017216 A1 | 1/2003 | Schmidt et al. |
| 2003/0050334 A1 | 3/2003 | Murty et al. |
| 2006/0078955 A1 | 4/2006 | Lin et al. |
| 2006/0135599 A1 | 6/2006 | Symonds et al. |
| 2006/0194761 A1 | 8/2006 | Gu |
| 2007/0077660 A1 | 4/2007 | Glas |
| 2007/0287843 A1 | 12/2007 | Cabaj et al. |
| 2008/0103193 A1 | 5/2008 | Castor et al. |
| 2008/0181942 A1 | 7/2008 | Zajicek |
| 2008/0221339 A1 | 9/2008 | Webster et al. |
| 2008/0312465 A1 | 12/2008 | Souza et al. |
| 2009/0042974 A1 | 2/2009 | Parker et al. |
| 2009/0197941 A1 | 8/2009 | Guy et al. |
| 2009/0306221 A1 | 12/2009 | Guy et al. |
| 2010/0292345 A1 | 11/2010 | Pertwee |
| 2010/0298579 A1 | 11/2010 | Steup et al. |
| 2011/0171300 A1 | 7/2011 | Bhatarah et al. |
| 2011/0257256 A1 | 10/2011 | Fuchs et al. |
| 2012/0144523 A1 | 6/2012 | Page et al. |
| 2013/0079531 A1 | 3/2013 | Barringer |
| 2013/0295172 A1 | 11/2013 | Freeman |
| 2014/0057251 A1 | 2/2014 | McKeman |
| 2014/0243405 A1 | 8/2014 | Whalley et al. |
| 2014/0271940 A1 | 9/2014 | Wurzer |
| 2014/0287067 A1 | 9/2014 | Velasco Diez et al. |
| 2015/0057342 A1 | 2/2015 | Koren et al. |
| 2015/0083146 A1 | 3/2015 | Goldman et al. |
| 2015/0126754 A1 | 5/2015 | Fernandez Cid et al. |
| 2015/0203434 A1 | 7/2015 | Flockhart et al. |
| 2015/0258153 A1 | 9/2015 | Rosenblatt et al. |
| 2016/0002579 A1 | 1/2016 | Rosenthal et al. |
| 2016/0018424 A1 | 1/2016 | Lucas et al. |
| 2016/0051510 A1 | 2/2016 | Allen et al. |
| 2016/0058866 A1 | 3/2016 | Sekura et al. |
| 2016/0143972 A1 | 5/2016 | Stebbins et al. |
| 2016/0158299 A1 | 6/2016 | Bohus |
| 2016/0177404 A1 | 6/2016 | McKeman |
| 2016/0228787 A1 | 8/2016 | Payack |
| 2016/0243460 A1 | 8/2016 | Leveson et al. |
| 2016/0279183 A1 | 9/2016 | Hospodor et al. |
| 2016/0298151 A1 | 10/2016 | Butt et al. |
| 2016/0324776 A1 | 11/2016 | Glatzel |
| 2016/0324777 A1 | 11/2016 | Victor et al. |
| 2016/0354561 A1 | 12/2016 | McCullough |
| 2016/0360721 A1 | 12/2016 | De Meijer |
| 2017/0008870 A1 | 1/2017 | Dibble et al. |
| 2017/0021029 A1 | 1/2017 | Raber et al. |
| 2017/0022132 A1 | 1/2017 | Mona, III et al. |
| 2017/0042835 A1 | 2/2017 | Singh |
| 2017/0079933 A1 | 3/2017 | Whittle et al. |
| 2017/0095518 A1 | 4/2017 | Bjorncrantz |
| 2017/0119728 A1 | 5/2017 | DeGeeter |
| 2017/0188605 A1 | 7/2017 | Franklin et al. |
| 2017/0196923 A1 | 7/2017 | Moore |
| 2017/0202896 A1 | 7/2017 | Hugh |
| 2017/0240840 A1 | 8/2017 | Privitera et al. |
| 2017/0252384 A1 | 9/2017 | Goldner |
| 2017/0290869 A1 | 10/2017 | Whittle et al. |
| 2017/0312652 A1 | 11/2017 | Love |
| 2017/0360861 A1 | 12/2017 | Humphreys et al. |
| 2017/0361525 A1 | 12/2017 | Warner et al. |
| 2017/0368021 A1 | 12/2017 | Atkinson et al. |
| 2018/0016203 A1 | 1/2018 | Raber et al. |
| 2018/0021247 A1 | 1/2018 | Ghalili et al. |
| 2018/0036278 A1 | 2/2018 | Rutz |
| 2018/0059128 A1 | 3/2018 | McDonald et al. |
| 2018/0064772 A1 | 3/2018 | Naheed |
| 2018/0071701 A1 | 3/2018 | Zhang et al. |
| 2018/0078593 A1 | 3/2018 | Naheed |
| 2018/0078874 A1 | 3/2018 | Thomas |
| 2018/0085684 A1 | 3/2018 | Crandall et al. |
| 2018/0092953 A1 | 4/2018 | Brazil |
| 2018/0094209 A1 | 4/2018 | Carberry |
| 2018/0098552 A1 | 4/2018 | Bhairam |
| 2018/0099017 A1 | 4/2018 | Jones |
| 2018/0116998 A1 | 5/2018 | Sinai et al. |
| 2018/0125777 A1 | 5/2018 | Lindsay |
| 2018/0140965 A1 | 5/2018 | Flora et al. |
| 2018/0143212 A1 | 5/2018 | Giese et al. |
| 2018/0147247 A1 | 5/2018 | Ivanov |
| 2018/0161285 A1 | 6/2018 | Mukunda et al. |
| 2018/0193399 A1 | 7/2018 | Kariman |
| 2018/0193403 A1 | 7/2018 | George et al. |
| 2018/0200316 A1 | 7/2018 | Bray et al. |
| 2018/0201560 A1 | 7/2018 | Kavarana et al. |
| 2018/0207213 A1 | 7/2018 | McElvany |
| 2018/0221304 A1 | 8/2018 | Small-Howard et al. |
| 2018/0224411 A1 | 8/2018 | Raber et al. |
| 2018/0228854 A1 | 8/2018 | Raderman |
| 2018/0236017 A1 | 8/2018 | Stoops |
| 2018/0237368 A1 | 8/2018 | Keller |
| 2018/0265803 A1 | 9/2018 | Cumings et al. |
| 2018/0271827 A1 | 9/2018 | Heimark et al. |
| 2018/0273501 A1 | 9/2018 | Robertson et al. |
| 2018/0280459 A1 | 10/2018 | Eyal |
| 2018/0282250 A1 | 10/2018 | Rutz et al. |
| 2018/0289665 A1 | 10/2018 | Turner et al. |
| 2018/0293672 A1 | 10/2018 | Johnson |
| 2018/0318361 A1 | 11/2018 | Eyal |
| 2018/0319763 A1 | 11/2018 | Dialer et al. |
| 2018/0333446 A1 | 11/2018 | Shan et al. |
| 2018/0334692 A1 | 11/2018 | Barr et al. |
| 2018/0343901 A1 | 12/2018 | Leo et al. |
| 2018/0344661 A1 | 12/2018 | Finley et al. |
| 2018/0344662 A1 | 12/2018 | Eyal et al. |
| 2018/0344785 A1 | 12/2018 | Robertson |
| 2018/0346866 A1 | 12/2018 | Peet et al. |
| 2018/0353463 A1 | 12/2018 | Winnicki |
| 2018/0361271 A1 | 12/2018 | Galyuk |
| 2018/0362429 A1 | 12/2018 | Zhang et al. |
| 2018/0369714 A1 | 12/2018 | Coffin |
| 2018/0369715 A1 | 12/2018 | Bruining |
| 2018/0369716 A1 | 12/2018 | Robbins et al. |
| 2018/0371507 A1 | 12/2018 | Poulos et al. |
| 2019/0000794 A1 | 1/2019 | Tanaka |
| 2019/0015383 A1 | 1/2019 | Woelfel et al. |
| 2019/0022054 A1 | 1/2019 | Greenbaum et al. |
| 2019/0023680 A1 | 1/2019 | Leahy et al. |
| 2019/0030062 A1 | 1/2019 | Mukunda et al. |
| 2019/0030100 A1 | 1/2019 | Hospodor et al. |
| 2019/0030102 A1 | 1/2019 | Scialdone |
| 2019/0037909 A1 | 2/2019 | Greenbaum et al. |
| 2019/0038995 A1 | 2/2019 | Tucker |
| 2019/0046440 A1 | 2/2019 | Kleidon et al. |
| 2019/0046499 A1 | 2/2019 | Segreti |
| 2019/0054394 A1 | 2/2019 | Hare |
| 2019/0060227 A1 | 2/2019 | Silver |
| 2019/0060381 A1 | 2/2019 | Ballan et al. |
| 2019/0060785 A1 | 2/2019 | Durward |
| 2019/0062144 A1 | 2/2019 | Greenbaum et al. |
| 2019/0070128 A1 | 3/2019 | Guy et al. |
| 2019/0076756 A1 | 3/2019 | Moore |

(56) References Cited

U.S. PATENT DOCUMENTS

| | | | |
|---|---|---|---|
| 2019/0077782 | A1 | 3/2019 | Raber et al. |
| 2019/0077783 | A1 | 3/2019 | Koch et al. |
| 2019/0083418 | A1 | 3/2019 | Guy et al. |
| 2019/0083902 | A1 | 3/2019 | Nevitt |
| 2019/0085279 | A1 | 3/2019 | Leo |
| 2019/0085347 | A1 | 3/2019 | Sayre et al. |
| 2019/0090515 | A1 | 3/2019 | Franklin et al. |
| 2019/0091144 | A1 | 3/2019 | McGarrah et al. |
| 2019/0091200 | A1 | 3/2019 | Tepper et al. |
| 2019/0099696 | A1 | 4/2019 | Ko et al. |
| 2019/0099736 | A1 | 4/2019 | Sibal |
| 2019/0105298 | A1 | 4/2019 | Eyal |
| 2019/0117617 | A1 | 4/2019 | Kariman |
| 2019/0117778 | A1 | 4/2019 | Leone-Bay et al. |
| 2019/0231737 | A1 | 8/2019 | Black |
| 2019/0270691 | A1 | 9/2019 | Black |
| 2019/0307695 | A1 | 10/2019 | Colvin |
| 2019/0382325 | A1 | 12/2019 | Black |
| 2019/0382326 | A1 | 12/2019 | Black |

FOREIGN PATENT DOCUMENTS

| | | | |
|---|---|---|---|
| AU | 2002218242 | | 7/2002 |
| AU | 2002229456 | | 3/2003 |
| AU | 2002255150 | | 5/2003 |
| AU | 2002319422 | | 5/2003 |
| AU | 2002365231 | | 9/2003 |
| AU | 2003205844 | | 9/2003 |
| AU | 2017334283 | | 4/2018 |
| AU | 2017341707 | | 4/2018 |
| AU | 2018100837 | | 7/2018 |
| AU | 2018253527 | | 11/2018 |
| AU | 2017296180 | | 1/2019 |
| AU | 2017301239 | | 3/2019 |
| AU | 2017313843 | | 3/2019 |
| BR | PI 0910426 | A2 | 8/2015 |
| BR | 112013012468 | A2 | 9/2016 |
| BR | 112016009872 | A2 | 8/2017 |
| BR | 112016030944 | A2 | 8/2017 |
| BR | 112017007767 | A2 | 1/2018 |
| BR | 112017019899 | A2 | 6/2018 |
| BR | 112018001310 | A2 | 9/2018 |
| BR | 112018005639 | A2 | 10/2018 |
| BR | 112018074859 | A2 | 12/2018 |
| BR | 112018005423 | A2 | 2/2019 |
| CA | 2348695 | | 5/2000 |
| CA | 2472561 | | 8/2002 |
| CA | 2469490 | | 7/2003 |
| CA | 2391454 | | 12/2003 |
| CA | 2504743 | | 5/2004 |
| CA | 2656698 | | 12/2007 |
| CA | 2751741 | | 8/2009 |
| CA | 2910206 | | 12/2015 |
| CA | 2937471 | | 9/2016 |
| CA | 2941961 | | 3/2018 |
| CA | 2997850 | | 5/2018 |
| CA | 2911168 | | 8/2018 |
| CA | 3000255 | | 9/2018 |
| CA | 2993834 | | 10/2018 |
| CA | 3024431 | | 1/2019 |
| CA | 3024645 | | 1/2019 |
| CA | 3013573 | | 2/2019 |
| CA | 3009554 | | 3/2019 |
| CH | 706963 | | 3/2014 |
| CN | 1560005 | | 1/2005 |
| CN | 100387230 | C | 5/2008 |
| CN | 101932314 | | 12/2010 |
| CN | 1962665 | | 5/2011 |
| CN | 1997636 | | 9/2011 |
| CN | 102766128 | | 11/2012 |
| CN | 103300073 | | 9/2013 |
| CN | 103417593 | | 12/2013 |
| CN | 103739585 | | 4/2014 |
| CN | 104031736 | | 9/2014 |
| CN | 104277917 | | 1/2015 |
| CN | 104302193 | A | 1/2015 |
| CN | 204111719 | | 1/2015 |
| CN | 104447673 | | 3/2015 |
| CN | 105505565 | | 4/2016 |
| CN | 105535111 | | 5/2016 |
| CN | 105935374 | | 9/2016 |
| CN | 105943613 | | 9/2016 |
| CN | 105943615 | | 9/2016 |
| CN | 105943617 | | 9/2016 |
| CN | 105943619 | | 9/2016 |
| CN | 105963359 | | 9/2016 |
| CN | 105997985 | | 10/2016 |
| CN | 105998192 | | 10/2016 |
| CN | 106074465 | | 11/2016 |
| CN | 106074496 | | 11/2016 |
| CN | 106074707 | | 11/2016 |
| CN | 106232130 | | 12/2016 |
| CN | 106265364 | | 1/2017 |
| CN | 106389535 | | 2/2017 |
| CN | 106632214 | | 5/2017 |
| CN | 106810426 | | 6/2017 |
| CN | 106860492 | | 6/2017 |
| CN | 206244694 | | 6/2017 |
| CN | 107011125 | | 8/2017 |
| CN | 107050001 | | 8/2017 |
| CN | 107050002 | | 8/2017 |
| CN | 107095302 | | 8/2017 |
| CN | 107337586 | | 8/2017 |
| CN | 107137604 | | 9/2017 |
| CN | 107227198 | | 10/2017 |
| CN | 107325881 | | 11/2017 |
| CN | 107344908 | | 11/2017 |
| CN | 107382672 | | 11/2017 |
| CN | 107382672 | A | 11/2017 |
| CN | 107589203 | | 1/2018 |
| CN | 107811904 | | 3/2018 |
| CN | 107898826 | | 4/2018 |
| CN | 108078965 | | 5/2018 |
| CN | 207384904 | | 5/2018 |
| CN | 207384906 | | 5/2018 |
| CN | 108126012 | | 6/2018 |
| CN | 207532828 | | 6/2018 |
| CN | 108314608 | | 7/2018 |
| CN | 207591325 | | 7/2018 |
| CN | 108354914 | | 8/2018 |
| CN | 108479098 | | 9/2018 |
| CN | 207886739 | | 9/2018 |
| CN | 108640820 | | 10/2018 |
| CN | 108654134 | | 10/2018 |
| CN | 108802240 | | 11/2018 |
| CN | 108929201 | | 12/2018 |
| CN | 108968071 | | 12/2018 |
| CN | 108998248 | | 12/2018 |
| CN | 109010638 | | 12/2018 |
| CN | 109053388 | | 12/2018 |
| CN | 208292897 | | 12/2018 |
| CN | 109200046 | | 1/2019 |
| CN | 109232191 | | 1/2019 |
| CN | 109363026 | | 2/2019 |
| CN | 109369344 | | 2/2019 |
| CN | 208500803 | | 2/2019 |
| CN | 109394836 | | 3/2019 |
| CN | 109419665 | | 3/2019 |
| CN | 109419851 | | 3/2019 |
| CN | 109475512 | | 3/2019 |
| CN | 109475586 | | 3/2019 |
| CN | 109498606 | | 3/2019 |
| CN | 109528583 | | 3/2019 |
| CN | 109568389 | | 4/2019 |
| CN | 109574810 | | 4/2019 |
| CN | 109593651 | | 4/2019 |
| EP | 494665 | | 7/1992 |
| EP | 1076653 | | 2/2001 |
| EP | 1633733 | | 3/2006 |
| EP | 1644349 | | 4/2006 |
| EP | 1803717 | | 7/2007 |
| EP | 1893191 | | 3/2008 |
| EP | 1896389 | | 3/2008 |
| EP | 2007376 | | 12/2008 |

(56) References Cited

FOREIGN PATENT DOCUMENTS

| | | |
|---|---|---|
| EP | 2037901 | 3/2009 |
| EP | 2044935 | 4/2009 |
| EP | 2146731 | 1/2010 |
| EP | 2332533 | 6/2011 |
| EP | 2444081 | 4/2012 |
| EP | 2968259 | 1/2016 |
| EP | 3028697 | 6/2016 |
| EP | 3041815 | 7/2016 |
| EP | 3067058 | 9/2016 |
| EP | 3119391 | 1/2017 |
| EP | 3206679 | 8/2017 |
| EP | 3247402 | 11/2017 |
| EP | 3253727 | 12/2017 |
| EP | 3274321 | 1/2018 |
| EP | 3310390 | 4/2018 |
| EP | 3429580 | 1/2019 |
| EP | 3439759 | 2/2019 |
| EP | 3442515 | 2/2019 |
| EP | 3442552 | 2/2019 |
| EP | 3445838 | 2/2019 |
| EP | 3446697 | 2/2019 |
| EP | 3449914 | 3/2019 |
| EP | 3449915 | 3/2019 |
| EP | 3449916 | 3/2019 |
| EP | 3452025 | 3/2019 |
| EP | 3452026 | 3/2019 |
| EP | 3452195 | 3/2019 |
| EP | 3454849 | 3/2019 |
| EP | 3455213 | 3/2019 |
| EP | 3463335 | 4/2019 |
| EP | 3471745 | 4/2019 |
| EP | 3471746 | 4/2019 |
| EP | 3472142 | 4/2019 |
| FR | 2966698 | 5/2012 |
| FR | 3062303 | 8/2018 |
| GB | 1481048 | 7/1977 |
| GB | 2381450 | 5/2006 |
| GB | 2393182 | 3/2007 |
| GB | 2432312 | 5/2007 |
| GB | 2450974 | 2/2012 |
| GB | 2494461 | 3/2013 |
| GB | 2492487 | 9/2015 |
| GB | 2527599 | 12/2015 |
| GB | 2495841 | 2/2016 |
| GB | 2531282 | 4/2016 |
| GB | 2542797 | 4/2017 |
| GB | 2557921 | 7/2018 |
| GB | 2560019 | 8/2018 |
| GB | 2487183 | 10/2018 |
| GB | 2530001 | 1/2019 |
| GB | 2564383 | 1/2019 |
| IN | 200502571 | 5/2007 |
| IN | 253746 B | 8/2007 |
| IN | 264549 B | 8/2007 |
| IN | 200704456 | 8/2007 |
| IN | 222132 B | 7/2008 |
| IN | 200900654 | 5/2009 |
| IN | 200907295 | 6/2010 |
| IN | 242112 B | 8/2010 |
| IN | 201409507 | 7/2015 |
| IN | 201507784 | 1/2016 |
| IN | 201617015721 A | 8/2016 |
| IN | 201737002171 A | 5/2017 |
| IN | 201717008714 A | 7/2017 |
| IN | 201727014697 A | 7/2017 |
| IN | 201737030087 A | 10/2017 |
| IN | 201504124 I3 | 11/2017 |
| IN | 201737039585 A | 12/2017 |
| IN | 201727039031 A | 4/2018 |
| IN | 201817041962 A | 12/2018 |
| IN | 201817042032 A | 12/2018 |
| IN | 201817039498 A | 2/2019 |
| JP | 04969767 | 1/2005 |
| JP | 06239976 | 11/2017 |
| JP | 06280489 | 2/2018 |
| KR | 141524 | 6/1998 |
| KR | 711951 | 5/2007 |
| KR | 1029306 | 4/2011 |
| KR | 2019033590 | 3/2019 |
| KR | 2019034576 | 4/2019 |
| KR | 2019035791 | 4/2019 |
| MA | 37112 | 8/2016 |
| MX | 2017005277 | 1/2018 |
| MX | 2017015647 | 8/2018 |
| RU | 2016129536 | 1/2018 |
| WO | 2005061480 | 7/2005 |
| WO | 2005120478 | 12/2005 |
| WO | 2006063109 | 6/2006 |
| WO | 2006133941 | 12/2006 |
| WO | 2007/144628 | 12/2007 |
| WO | 2009013506 | 1/2009 |
| WO | 2012160358 | 11/2012 |
| WO | 2013006953 | 1/2013 |
| WO | 2015032519 | 3/2015 |
| WO | 2015122484 | 8/2015 |
| WO | 2015/191728 | 12/2015 |
| WO | 2016/004410 | 1/2016 |
| WO | 2016/092376 | 6/2016 |
| WO | 2016116628 | 7/2016 |
| WO | 2016/127111 | 8/2016 |
| WO | 2016/138505 | 9/2016 |
| WO | 2016/147186 | 9/2016 |
| WO | 2016/0153347 | 9/2016 |
| WO | 2016/154032 | 9/2016 |
| WO | 2016/161420 | 10/2016 |
| WO | 2016160542 | 10/2016 |
| WO | 2016/179581 | 11/2016 |
| WO | 2016/187679 | 12/2016 |
| WO | 2016/189384 | 12/2016 |
| WO | 2016205923 | 12/2016 |
| WO | 2017/011210 | 1/2017 |
| WO | 2017/051398 | 3/2017 |
| WO | 2017048750 | 3/2017 |
| WO | 2017139496 | 8/2017 |
| WO | 2017175064 | 10/2017 |
| WO | 2018048952 | 3/2018 |
| WO | 2018061007 | 4/2018 |
| WO | 2018061009 | 4/2018 |
| WO | 2018064654 | 4/2018 |
| WO | 2018065479 | 4/2018 |
| WO | 2018071372 | 4/2018 |
| WO | 2018071452 | 4/2018 |
| WO | 2018083695 | 5/2018 |
| WO | 2018089863 | 5/2018 |
| WO | 2018102711 | 6/2018 |
| WO | 2018106973 | 6/2018 |
| WO | 2018112329 | 6/2018 |
| WO | 2018113888 | 6/2018 |
| WO | 2018125857 | 7/2018 |
| WO | 2018130682 | 7/2018 |
| WO | 2018142403 | 8/2018 |
| WO | 2018152637 | 8/2018 |
| WO | 2018160510 | 9/2018 |
| WO | 2018163187 | 9/2018 |
| WO | 2018167038 | 9/2018 |
| WO | 2018170596 | 9/2018 |
| WO | 2018175796 | 9/2018 |
| WO | 2018183115 | 10/2018 |
| WO | 2018187500 | 10/2018 |
| WO | 2018195562 | 10/2018 |
| WO | 2018200888 | 11/2018 |
| WO | 2018204326 | 11/2018 |
| WO | 2018204859 | 11/2018 |
| WO | 2018205038 | 11/2018 |
| WO | 2018209425 | 11/2018 |
| WO | 2018211388 | 11/2018 |
| WO | 2018215520 | 11/2018 |
| WO | 2018222923 | 12/2018 |
| WO | 2018233991 | 12/2018 |
| WO | 2018234301 | 12/2018 |
| WO | 2018235079 | 12/2018 |
| WO | 2019002933 | 1/2019 |
| WO | 2019003226 | 1/2019 |
| WO | 2019011664 | 1/2019 |

(56) References Cited

FOREIGN PATENT DOCUMENTS

| | | |
|---|---|---|
| WO | 2019012267 | 1/2019 |
| WO | 2019014490 | 1/2019 |
| WO | 2019020738 | 1/2019 |
| WO | 2019023668 | 1/2019 |
| WO | 2019023751 | 2/2019 |
| WO | 2019023803 | 2/2019 |
| WO | 2019030561 | 2/2019 |
| WO | 2019032150 | 2/2019 |
| WO | 2019032609 | 2/2019 |
| WO | 2019034936 | 2/2019 |
| WO | 2019043259 | 3/2019 |
| WO | 2019045994 | 3/2019 |
| WO | 2019046806 | 3/2019 |
| WO | 2019049142 | 3/2019 |
| WO | 2019051560 | 3/2019 |
| WO | 2019052830 | 3/2019 |
| WO | 2019057994 | 3/2019 |
| WO | 2019063848 | 4/2019 |
| WO | 2019064031 | 4/2019 |
| WO | 2019069309 | 4/2019 |
| WO | 2019070885 | 4/2019 |
| WO | 2019071000 | 4/2019 |
| WO | 2019071302 | 4/2019 |
| WO | 2019079208 | 4/2019 |

OTHER PUBLICATIONS

Straight, R., et al., "Marihuana extraction and purification for oral administration of known amounts of delta9-tetrahydrocannabinol (THC)", 1973, Biochemical Medicine, No. 8, pp. 341-344 (Year: 1973).

* cited by examiner

SYNTHESIS OF CANNABIGEROL

CLAIM OF PRIORITY

This application claims priority to U.S. Patent Application No. 62/743,982, filed Oct. 10, 2018, which is incorporated by reference herein in its entirety.

BACKGROUND

Cannabigerol ("CBG") is one of the many non-psychoactive cannabinoids naturally produced in a variety of strains of *Cannabis sativa*. Researchers are hopeful that CBG will provide many pharmacological, medicinal, and therapeutic benefits. For example, initial research indicates that CBG may be effective in reducing intraocular pressure, reducing tissue inflammation, inhibiting bacterial growth, and blocking cancer related intracellular growth receptors. Further research, however, remains necessary to test the efficacy of CBG with respect to these and other benefits.

Current *Cannabis sativa* plant strains ("*cannabis* plants"), however, contain limited amounts of CBG. During the growth phase of the *cannabis* plant, most CBG is converted into other cannabinoids, such as cannabidiol and tetrahydrocannabinol. As a result, most *cannabis* plants contain less than one percent ("1%") of CBG. Extracting CBG and isolating CBG from *cannabis* plants has the potential to further denature the CBG contained in *cannabis* plants.

Synthetic methods to produce CBG, while known, suffer from low yields and long reaction times. Additionally, known methods produce undesired products. As a result, current technology limits the amount of CBG available for testing, and the available CBG is prohibitively expensive. Thus, it remains desirous to develop technologies that provide an easier, cheaper, and more effective method to produce relatively pure isolated CBG.

It is with respect to these and other considerations that the technology is disclosed. Also, although relatively specific problems have been discussed, it should be understood that the embodiments presented should not be limited to solving the specific problems identified in the introduction.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

Aspects of the present technology relate to the production of cannabigerol through various synthetic means. For example, aspects of the technology relate to reacting geraniol-derivatives with olivetol in a solvent to form cannabigerol. In alternative/additional aspects, no solvent is used.

Additional/alternative aspects of the technology relate to adding one or more catalysts including one or more of p-toluenesulfonic acid ("pTSA"), camphorsulfonic acid ("CSA"), trifluoroacetic acid ("TFA"), acetic acid ("AcOH"), formic acid, boron triflouride ("BF$_3$"), Zinc Bromide ("ZnBr$_2$"), methanesulfonic acid ("MsOH"), iron (III) chloride ("FeCl3"), hydrochloric acid, and acetyl chloride ("AcCl"). Other catalysts are described herein.

In aspects of the technology, the solvent may be one or more of methyl tert-butyl ether ("MTBE"), acetonitrile, toluene, ethanol, heptane, hexane, pentane, acetone, ethyl acetate, butyl acetate, isobutyl acetate, t-butyl acetate, tetrahydrofuran, 2-methyl tetrahydrofuran, tetrahydrofuran, 1,4-dioxane, chloroform, or dichloromethane.

The olivetol and cannabigerol-derivative may be dissolved in the solvent in a relative molar ratio. In aspects of the technology, the relative molar ratio is a 1:1 molar ratio of olivetol and cannabigerol-derivative. Each may be in solution in a relative molar concentration, such as 0.5, 1, 2, 5, or 10 molar concentration.

The temperature, residence time, reactants, catalysts, solvents (if any), and concentrations may be selected to control the rate of the reaction, the conversion of CBG (a percentage calculated by the amount of observed CBG (mols) divided by the starting amount of olivetol (mols)), and/or the production of other by products.

To obtain CBG from the resulting solution, one or more techniques may be employed to separate and/or isolate CBG. For example, a base may be added to the solution to neutralize the solution (e.g., sodium bicarbonate), and a desiccant may be added, such as magnesium sulfate. Vacuum filtration, falling film distillation, and/or chromatography (such as column chromatrography) may be employed, which yields an oil that includes CBG.

Aspects of the technology further include obtaining CBG through cross coupling.

Further aspects of the technology include a compound having the formula:

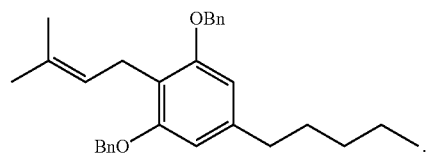 [SMILES: CCCCCc1cc(OCc2ccccc2)c(CC=C(C)C)c(OCc2ccccc2)c1]

Further aspects of the technology include a compound having the formula:

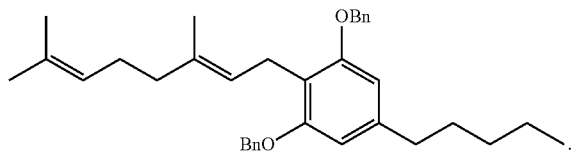

Further aspects of the technology include a compound having the formula:

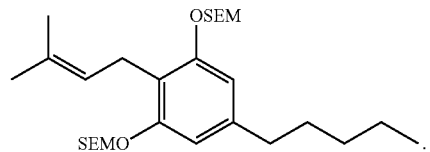

Further aspects of the technology include a compound having the formula:

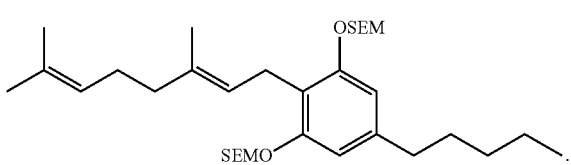

Further aspects of the technology include a compound having the formula:

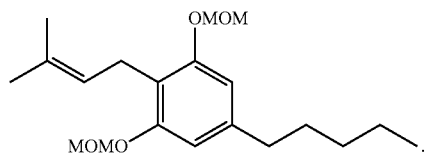

Further aspects of the technology include a compound having the formula:

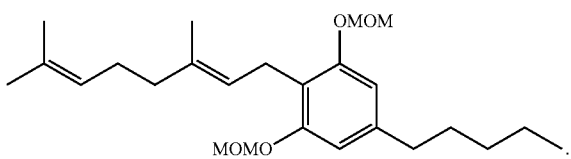

Aspects of the technology include a method of making CBG, the method include providing a solvent, adding olivetol to the solvent, adding geraniol-derivative to the solvent, wherein the generiol-derivative has the formula:

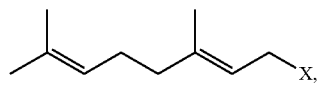

where X is OH or bromide, adding an acidic catalyst to the solvent to form a solution; and reacting the solution to form a reactant solution comprising CBG.

Further aspects of the technology include a method comprising:
providing a first compound having the structure

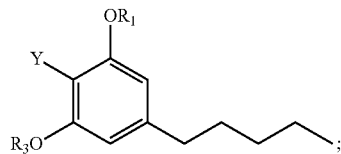

combining the first compound with a second compound having the structure:

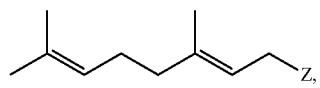

in a solvent to form a solution; adding a catalyst to the solution to form an active mixture; and reacting the active mixture to form a reacting mixture, wherein the reacting mixture contains a detectable amount of a third compound having the structure:

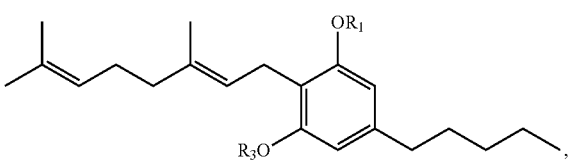

wherein $R_1$ and $R_3$ each are selected from the group consisting of: SEM, MOM, Me, Bn, TBS, and hydrogen; wherein Z is selected from the group consisting of: boronate group, boronic acid, iodide, and bromide; and wherein Y is selected from the group consisting of: iodide, bromide, Bpin, a boronate group and boronic acid group.

Further aspects of the technology include a method comprising: providing a first compound having the structure

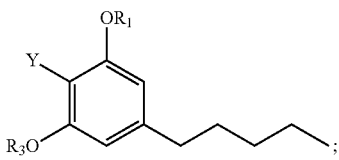

combining the first compound with a second compound having the structure:

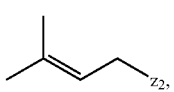

in a solvent to form a solution; adding a catalyst to the solution to form an active mixture; and reacting the active mixture to form a reacting mixture, wherein the reacting mixture contains a detectable amount of a third compound having the structure

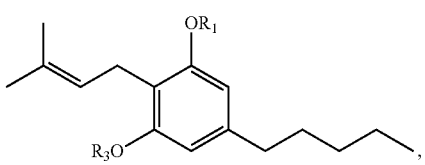

wherein $R_1$ and $R_3$ each are selected from the group consisting of: SEM, MOM, Me, Bn, TBS, and hydrogen, wherein $Z_2$ is selected from the group consisting of: boronate group, boronic acid, iodide, bromide, wherein Y is selected from the group consisting of: iodide, bromide, Bpin, a boronate group and boronic acid group.

BRIEF DESCRIPTION OF THE DRAWINGS

The following drawing figures, which form a part of this application, are illustrative of aspects of systems and methods described below, and are not meant to limit the scope of the disclosure in any manner, which scope shall be based on the claims.

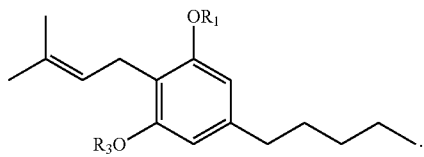

(Formula VI)

DETAILED DESCRIPTION

The terminology used in this disclosure is for the purpose of describing particular embodiments only and is not intended to be limiting of the disclosure. As used in the description of the embodiments of the disclosure and the appended claims, the singular forms "a," "an," and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Unless otherwise indicated, a used herein, the following structures have the names indicated below the structure:

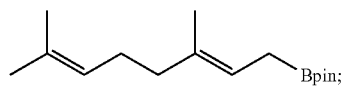

Geranyl Bpin

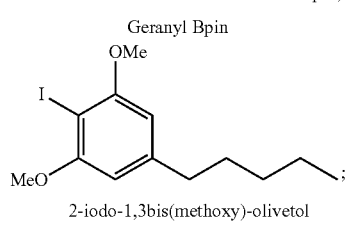

2-iodo-1,3bis(methoxy)-olivetol

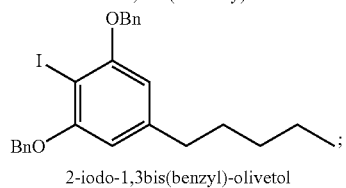

2-iodo-1,3bis(benzyl)-olivetol

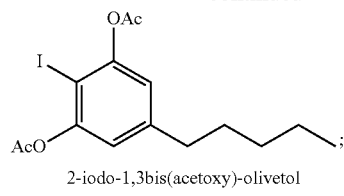

2-iodo-1,3bis(acetoxy)-olivetol

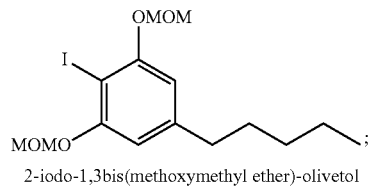

2-iodo-1,3bis(methoxymethyl ether)-olivetol

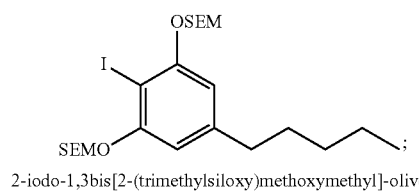

2-iodo-1,3bis[2-(trimethylsiloxy)methoxymethyl]-olivetol

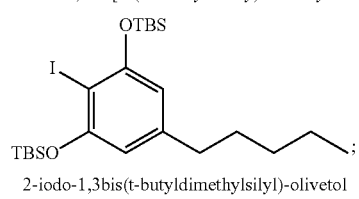

2-iodo-1,3bis(t-butyldimethylsilyl)-olivetol

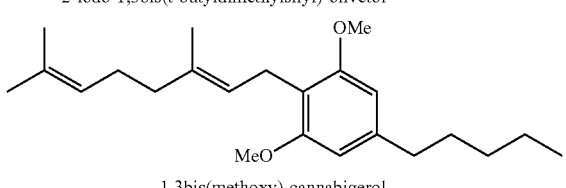

1,3bis(methoxy)-cannabigerol

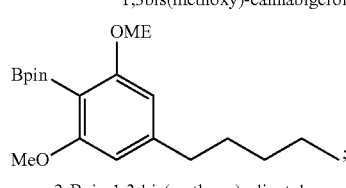

2-Bpin-1,3-bis(methoxy)-olivetol

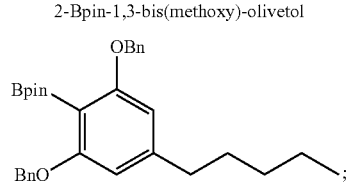

2-Bpin-1,3-bis(benzyl)-olivetol

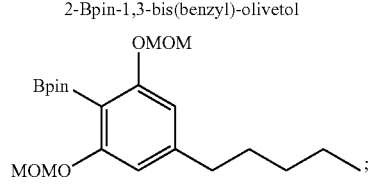

2-Bpin-1,3-bis(methoxymethyl ether)-olivetol

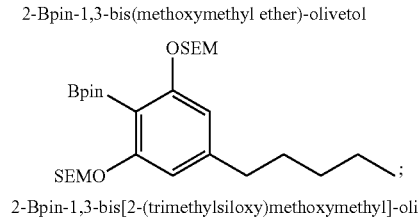

2-Bpin-1,3-bis[2-(trimethylsiloxy)methoxymethyl]-olivetol

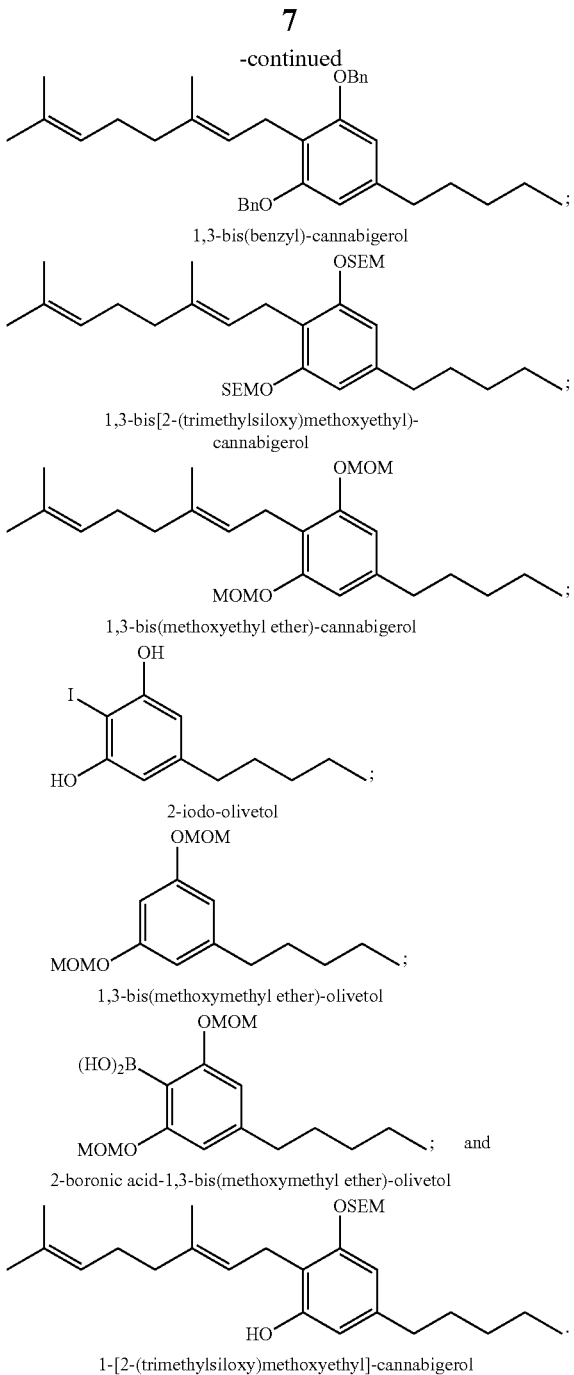

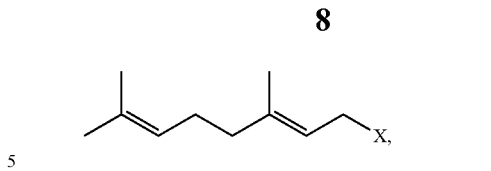

where X may be OH or bromide, ("Formula I") with olivetol having the formula of:

to form CBG having the formula of

In aspects of the technology, reacting olivetol with geraniol-derivatives forms a compound having the formula (hereinafter referred to as "Compound B") and/or (hereinafter referred to as "Compound C"). As will be appreciated through this disclosure, the selection of the reactants, solvents, catalysts, residence time, and/or temperature may affect the conversion of CBG, Compound B, and Compound C.

Figure 1:
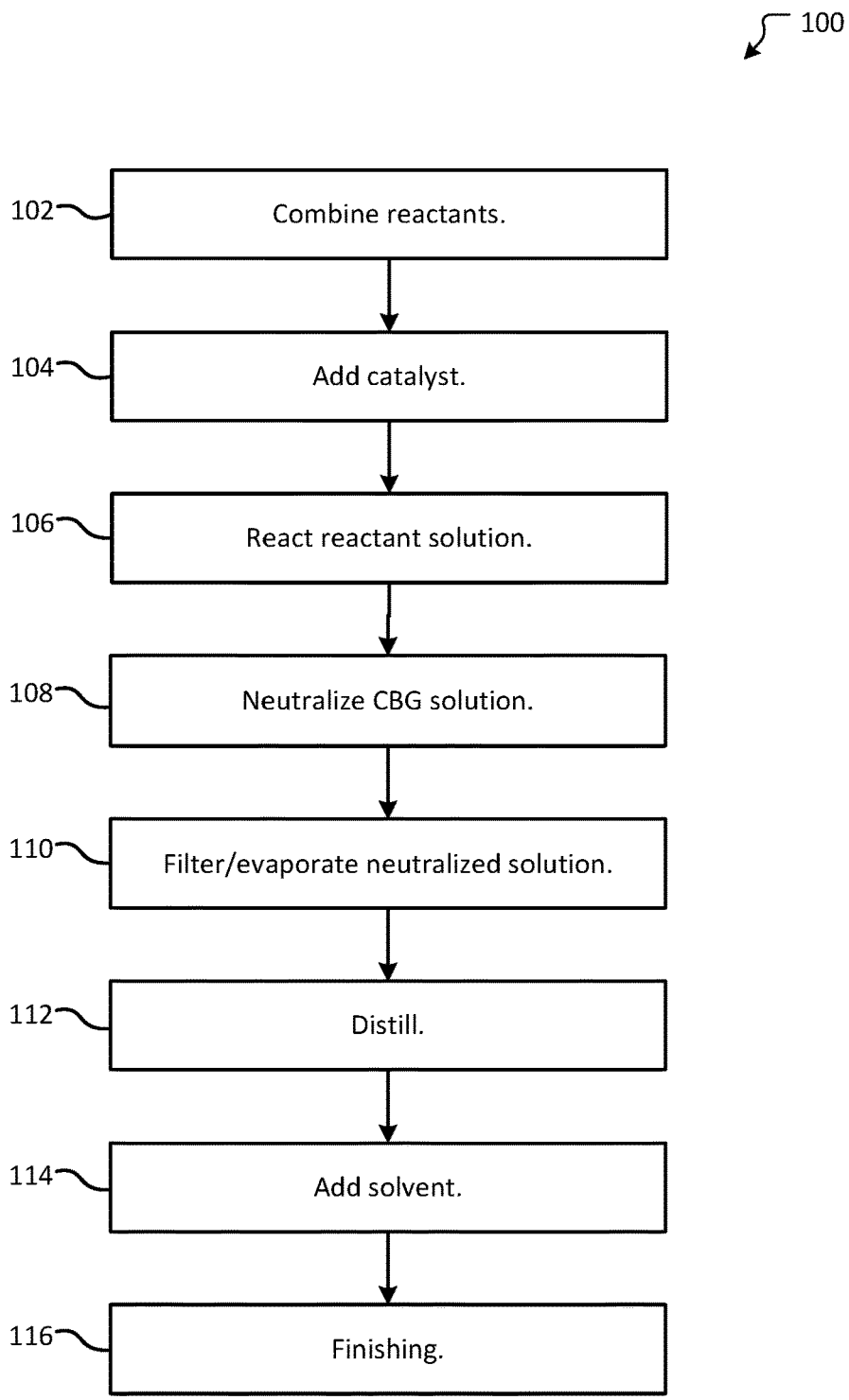
FIG. 1 is a method of synthesizing cannabigerol.

FIG. 1 provides a method 100 of synthesizing CBG using the geraniol-derivative of Formula I and olivetol. Method 100 begins with combining reactants operation 102. In aspects of the technology, the geraniol-derivative of Formula I and olivetol may be combined using a suitable solvent. In aspects of the technology, the molar ratio of olivetol and geraniol-derivative of Formula is around 1:1. Additionally/alternatively, the concentration of the resulting solution is around 1-10 M. In some aspects of the technology, the solvent may be one of methyl tert-butyl ether ("MTBE"), acetonitrile, toluene, ethanol, heptane, hexane, pentane, acetone, ethyl acetate, butyl acetate, isobutyl acetate, t-butyl acetate, tetrahydrofuran, 2-methyl tetrahydrofuran, tetrahydrofuran, 1,4-dioxane, chloroform, or dichloromethane or any combination of thereof. In other aspects of the technology, no solvent is use. Rather, the geraniol-derivative of Formula I and olivetol may be combined directly under an inert atmosphere, such as nitrogen. This forms a reactant mixture.

Method 100 then optionally proceeds to add catalyst operation 104. In operation 104, one or more suitable catalysts may be added to the reactant mixture. Suitable catalysts include at least one of: boron trifluoride, aluminium oxide, silicon dioxide, montmorillonite, magnesium sulfate, p-toluenesulfonic acid, camphorsulfonic acid, methanesulfonic acid, trifluoroacetic acid, acetic acid, formic acid, boron trifluoride, zinc(II) bromide, ferrous chloride, hydrochloric acid, silver nitrate, lithium carbonate, sodium carbonate, potassium carbonate, cesium carbonate, tetra-n-butylammonium bromide, silver nitrate, camphorsulfonic acid, methanesulfonic acid, hydrochloric acid, acetyl chloride and any combination thereof. This produces a catalyst-reactant mixture.

Method 100 then proceeds to react reactant solution operation 106. In operation 106, the reactant mixture (or the catalyst-reactant mixture) is heated or cooled to a temperature ("the Set Temperature"). The reactant mixture may be stirred and held at about the Set Temperature for a duration ("Residence Time"). For example, the reactant mixture may be kept at about 0° C., room temperature (about 23° C.), about 35° C., about 45° C., about 65° C., about 150° C. or any other temperature between 0° C. and 150° C. In other embodiments, the temperature may be maintained within +/−5° C. of any temperature between 0° C. and 100° C. This temperature may be maintained for 5 minutes to 48 hours in order to achieve a desired conversion rate of reactants into CBG, Compound B, or Compound C, or other compounds as desired. For example, the time may be maintained within +/−5, 10, or 15 minutes of any time between 5 minutes and 48 hours. The resulting mixture is a solution that includes CBG where a solvent is used or is a CBG mixture where no solvent is used.

Method 100 then optionally proceeds to the neutralize CBG solution operation 108. In operation 108, the CBG solution may be neutralized using a suitable neutralizing agent. For example, where the CBG solution is acidic, a base may be added such as sodium bicarbonate or potassium carbonate. In aspects of the technology, the base may be added in equal parts by weight to the acid in the solution. As a specific example, where para-toluenesulfonic acid was used as a catalyst, sodium bicarbonate or potassium carbonate may be added in a one weight relative weight percentage to the para-toluenesulfonic acid. Additionally/alternatively, the solution solvent may be washed using an appropriate wash, such as a saturated aqueous sodium bicarbonate or 1% aqueous potassium hydroxide wash. A desiccant, such as magnesium sulfate, sodium sulfate, or calcium chloride may be added. This forms a neutralized solution.

Method 100 then optionally proceeds to filter/evaporate neutralized solution operation 110. In operation 110, the neutralized solution is filtered to remove solid particulates. The solvent of the neutralized solution may then be evaporated off using a rotovap or any other technology now known or later developed. This forms a concentrated oil that comprises CBG.

In aspects of the technology, method 100 optionally proceeds to distill operation 112. In distill operation 112, the concentrated oil may be distilled using falling film distillation. For example, using a wiped falling film distillation unit, the residue may be distilled with an internal core temperature of 70° C. and outer wall temperature of 140° C., with a vacuum between 200 and 300 mtorr. This removes excess geraniol and geraniol by-products, as well as olivetol. The fraction with the highest boiling point (residue side) is collected. This forms a distilled concentrated oil.

Method 100 then proceeds to add solvent operation 114. In operation 114, the concentrated oil (or distilled concentrated oil) may then be combined with a suitable lipophilic solvent, such as benzene, heptane, acetic acid, acetone, isobutyl acetate, anisole, isopropyl acetate, 1-butanol, methyl acetate, 2-butanol, 3-methyl-1-butanol, butyl acetate, methylethylketone, tert-butylmethyl ether, methylisobutylketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, and any other suitable solvents now known or later developed. This forms a reactant oil.

Optionally, the method 100 proceeds to finishing operation 116. In finishing operation 116, the reactant oil may be chromatographed and/or chilled. For example, chromatography may proceed using a silica plug (3 g of silica for every 1 gram of oil, for example) and a 5% tert-butylmethyl ether in heptane as the eluent. In some aspects of the technology, around 30 mL of eluent for each gram of oil is used to collect 1 fraction. The solvent may then be removed under reduced pressure. The reactant oil and/or the fraction may then be chilled to precipitate out CBG. In aspects of the technology, the CBG is chilled to between −80 to −10° C.

Cross-Coupling Olivetol-Derivatives

Additional aspects of the technology relate to combining a 2-position modified olivetol-derivative having the formula of:

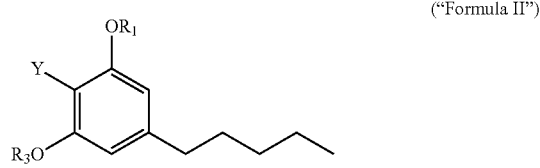

("Formula II")

where Y may be one of iodide, bromide, Bis(pinacolato) diboron pinacol boronate ("Bpin"), other boronates and boronic acids, and $R_1$ and $R_3$ each may be one of hydrogen, 2-(Trimethylsilyl)ethoxy]methyl acetal ("SEM"), methoxymethyl acetal ("MOM"), methyl ("Me"), benzyl ("Bn") or other ethers, tert-butyl(dimethyl)silyl ("TBS") or other silyl groups, acetate or other esters, with a suitable cross coupling agent having the formula of:

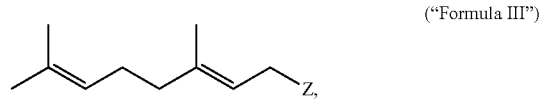

("Formula III")

where Z may be a boronate group, boronic acid, iodide, bromide, in the presence of one or more solvents and/or catalysts to produce CBG or a molecule a protected cannabigerol derivative having the formula:

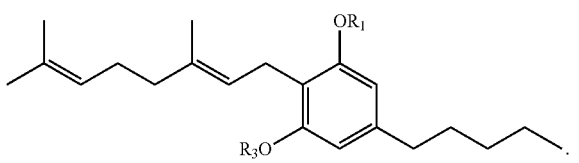

("Formula IV")

Figure 2:
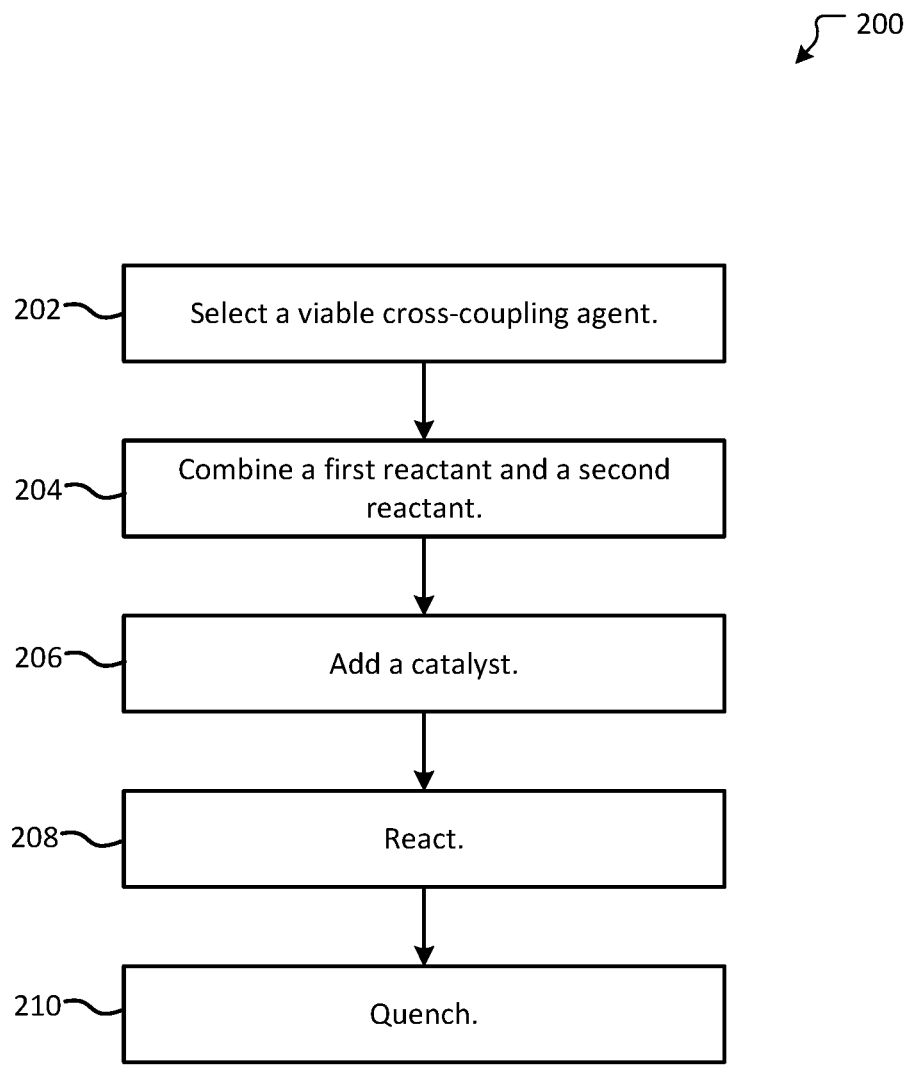
FIG. 2 is a method of synthesizing canabigerol using a cross-coupling method.

FIG. 2 provides a method 200 of synthesizing CBG (or a protected CBG-derivatives, e.g., with protecting groups at the 1 and 3 position of the resorcinol) using cross coupling methods. Method 200 begins with providing first reactant operation 202. In operation 202, a first reactant having the chemical formula

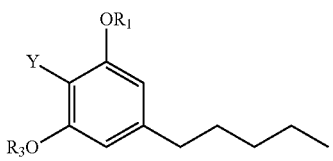

(described above, i.e., Formula II) is provided. In aspects of the technology Y may be a nucleophile, such as Bpin, other boronates or boronic acid or may be an electrophile such as Br or I. $R_1$ and $R_3$ may be a protecting group such as SEM, MOM, Me, Bn or other ethers, TBS or other silyl groups, acetate or other esters, or may be a hydrogen.

Method 200 then proceeds to select viable cross-coupling agent (i.e., the second reactant) having the formula of

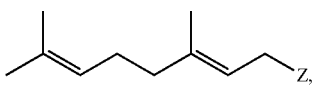

i.e., Formula III. In aspects of the technology, selection is made based on the first reactant provided in operation 202. For example, where Y is a nucleophile, Z may be selected to be an electrophile, and vice versa. For example, where Y is Bpin, Z may be bromide. In other examples, where Y is bromide, Z may be bpin.

Method 200 then proceeds to combine the first reactant and the second reactant 204. In operation 204, the first reactant and the second reactant are combined. The first reactant and second reactant may be combined in the presense of a solvent. Example solvents include N,N-dimethylacetamide, toluene, 1-butanol, and tetrahydrofuran or any other suitable solvent. This forms a solution.

Method 200 then proceeds to add catalyst operation 206. In aspects of the technology, a suitable catalyst. Suitable catalysts include XPhos-Pd-G3 ((2-Dicyclohexylphosphino-2',4',6'-triisopropyl-1,1'-biphenyl) [2-(2'-amino-1,1'-biphenyl)]palladium(II) methanesulfonate); SPhos-Pd-G2 (Chloro(2-dicyclohexylphosphino-2',6'-dimethoxy-1,1'-biphenyl) [2-(2'-amino-1,1'-biphenyl)]palladium(II)); cataCXium-A-Pd-G3-(Mesylate[(di(1-adamantyl)-n-butylphosphine)-2-(2'-amino-1,1'-biphenyl)]palladium(II)); APhos-Pd-G3 ([4-(Di-tert-butylphosphino)-N,N-dimethylaniline-2-(2'-aminobiphenyl)]palladium(II) methanesulfonate); P(Cy)3-Pd-G3 ([(Tricyclohexylphosphine)-2-(2'-aminobiphenyl)]palladium(II) methanesulfonate); PEPPSI-IPent (Dichloro[1,3-bis(2,6-Di-3-pentylphenyl) imidazol-2-ylidene](3-chloropyridyl)palladium(II)); and/or Pd(PPh3)4 (Palladium-tetrakis(triphenylphosphine)); or any combination thereof. This forms an active mixture.

Method 200 then proceeds to react operation 208. In react operation 210, the active mixture may be agitated (e.g., stirred) and/or heated/cooled for a certain duration. For example, the active mixture may be heated to 60° C. and held at that temperature for around 1 hour to around 48 hours. This forms a reacting mixture. The reacting mixture may contain detectable amounts of Formula IV.

Method 200 then proceeds to quench operation 210. In quench operation 210, the reaction is quenched. This may include cooling the reacting mixture, neutralizing the reacting mixture, and/or diluting the reacting mixture with suitable agents. This forms a quenched solution. The quenched solution may contain detectable amounts of Formula IV.

Cross-Coupling Olivetol-Derivatives with Prenyl Groups

Additional aspects of the technology relate to combining a 2-position modified olivetol-derivative having the formula of:

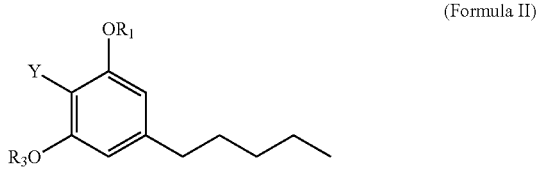

(Formula II)

where Y may be one of iodide, bromide, Bpin, other boronates and boronic acids, and $R_1$ and $R_3$ each may be one of hydrogen, SEM, MOM, Me, Bn or other ethers, TBS or other silyl groups, acetate or other esters, may be reacted a suitable cross coupling agent having the formula of:

("Formula V")

where $Z_2$ may be Bpin, other boronates, boronic acid, iodide, bromide, in the presence of one or more solvents and/or catalysts to produce CBG or a protected compound having the formula:

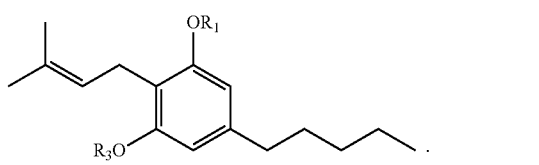

("Formula VI")

Figure 3:
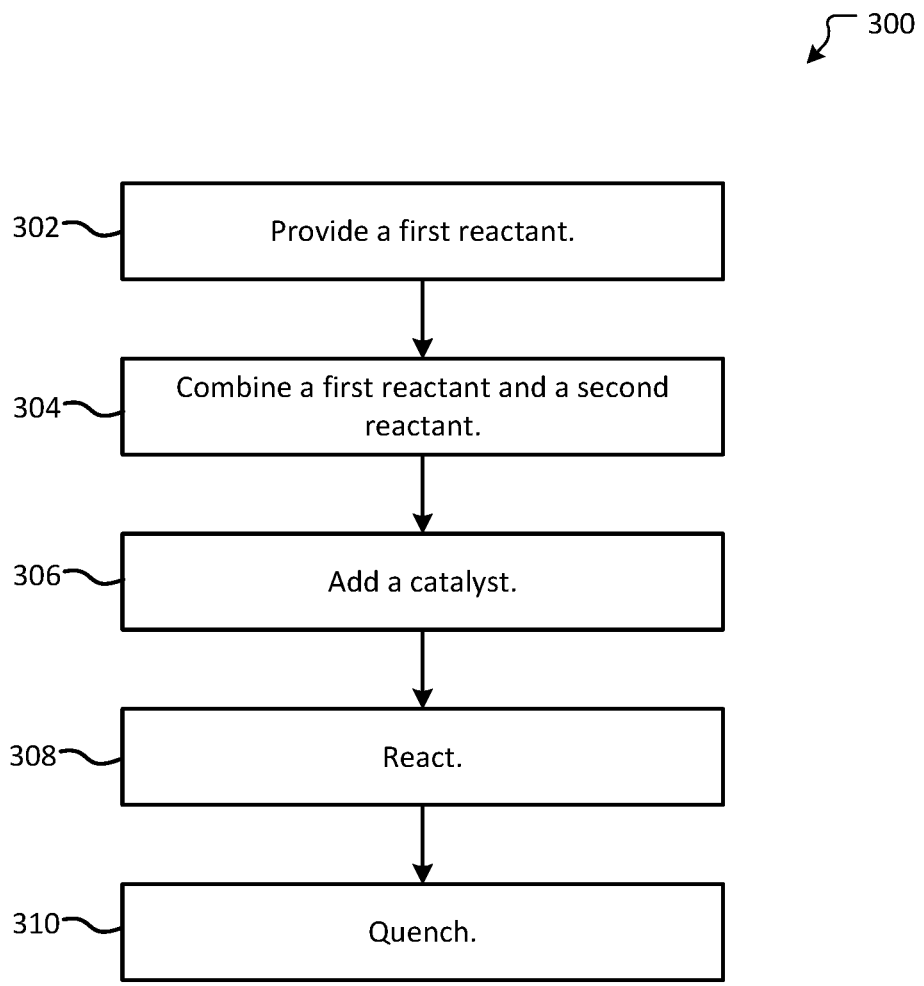
FIG. 3 provides a method 300 of synthesizing a compound having a Formula.

FIG. 3 provides a method 300 of synthesizing a compound having the formula:

(Formula VI)

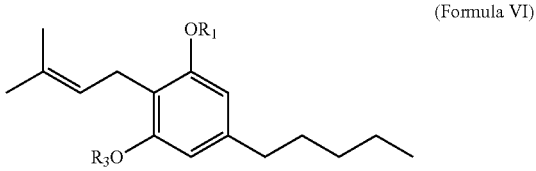

using cross coupling methods. Method 300 begins with providing first reactant operation 302. In operation 302, a first reactant having the chemical formula

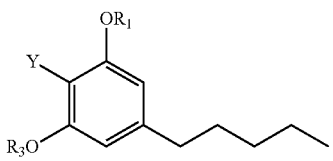

(described above, i.e., Formula II) is provided. In aspects of the technology Y may be a nucleophile, such as Bpin, other boronates or boronic acid or may be an electrophile Br or I. $R_1$ and $R_3$ may be a protecting group such as SEM, MOM, Me, Bn or other ethers, TBS or other silyl groups, acetate or other esters, or may be a hydrogen.

Method 300 then proceeds to select viable cross-coupling agent (i.e., the second reactant) having the formula of

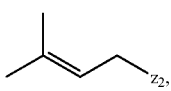

i.e., Formula V. In aspects of the technology, selection is made based on the first reactant provided in operation 302. For example, where Y is a nucleophile, $Z_2$ may be selected to be an electrophile. For example, where Y is Bpin, $Z_2$ may be bromide. In other examples, where Y is bromide, $Z_2$ may be bpin.

Method 300 then proceeds to combine the first reactant and the second reactant 304. In operation 304, the first reactant and the second reactant are combined. The first reactant and second reactant may be combined in the presence of a solvent. Example solvents include N,N-dimethylacetamide, toluene, 1-butanol, and tetrahydrofuran or any other suitable solvent. This forms a solution.

Method 300 then proceeds to add catalyst operation 306. In aspects of the technology, a suitable catalyst. Suitable catalysts include XPhos-Pd-G3, SPhos-Pd-G2, cataCXium-A-Pd-G3, APhos-Pd-G3, P(Cy)$_3$-Pd-G3, and PEPPSI-IPent. This forms an active solution.

Method 300 then proceeds to react operation 308. In react operation 308, the active solution may be agitated (e.g., stirred) and/or heated/cooled for a certain duration. For example, the active solution may be heated to 60° C. and held at that temperature for around 1 hour to around 48 hours. This forms a reacting solution.

Method 300 then proceeds to quench operation 310. In quench operation 310, the reaction is quenched. This may include cooling the reacting solution, neutralizing the reacting solution, and/or diluting the reacting solution with suitable agents. This forms a quenched solution. The quenched solution may contain detectable amounts of Formula VI.

Reactant Prep

Aspects of the technology relate to various preparations of reactants used for the technology described herein. For example, the compound of Formula II having the structure:

(Formula II)

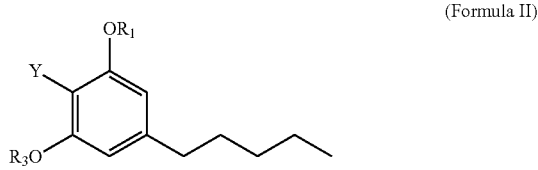

may be formed by reacting a compound having the formula (Formula VII)

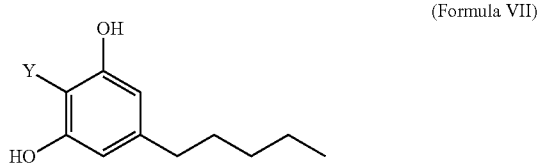

with a suitable reactant having the formula:

   (Formula VIII)

to form

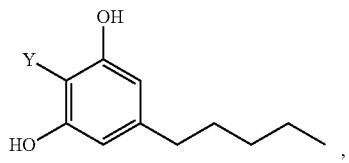

where $R_1$ and $R_3$ are the same, and each may be selected from the group consisting of SEM, MOM, Me, Bn or other ethers, TBS or other silyl groups, acetate or other esters. $Z_3$ may be one of chloride, bromide, iodide, triflate or suitable leaving groups. The reaction may take place in a suitable solvent such as methyl chloride, tetrahydrofuran, toluene or any other suitable solvent now known or later developed. A catalyst may be used such as Diisopropylethylamine ("DIPEA") or triethylamine, potassium carbonate, or any suitable base. The reaction may be run at −78° C. or 100° C. (or any temperature within that range within +/−2, 5, 10, or 15° C.) for a period of anywhere between 15 minutes to 48 hours+/−15 minutes.

Further aspects of the technology relate to modifying a compound having the formula (Formula IX)

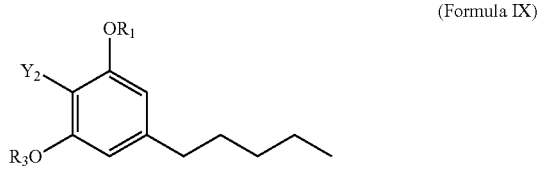

where $Y_2$ is an electrophile such as iodide ("I"), bromide ("Br"), or chloride (Cl) to form a compound:

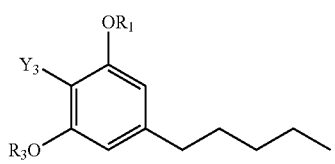

(Formula X)

where Y3 is a nucleophile. It will be appreciated that both Formula IX and Formula X are subsets of Formula II. In aspects, a compound having the formula:

Y₃—H (Formula XI)

is combined with a compound having the Formula IX in the presence of a suitable solvent such as THF toluene, any suitable solvent or any combination thereof. A catalyst may be used such as DIPEA triethylamine, potassium carbonate or any suitable base (or combination thereof). The reaction may be run at −78° C. or 100° C. (or any temperature within that range within +/−2, 5, 10, or 15° C.) for a period of anywhere between 15 minutes to 48 hours within +/− of 15 minutes.

CBG Deprotection

Aspects of the technology relate to removing protecting groups for a protected CBG-derivative. For example, a compound having the formula:

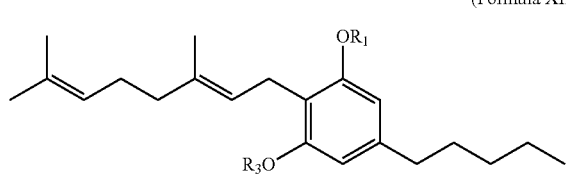

(Formula XII)

where the label $R_1$ and $R_3$ are protecting groups such as SEM, MOM, Me, Bn or other ethers, TBS or other silyl groups, acetate or other esters may be converted into CBG.

In aspects, certain protecting groups can be removed by dissolving the protected CBG in an organic solvent and treating with an acid such as methanolic hydrochloric acid, methane sulfonic acid, boron triflouride or any other suitable acid. In additional/alternative aspects, certain groups can be removed by dissolving the protected CBG in an organic solvent and treating with tetrabutylammonium fluoride. In additional, alternative aspects, certain groups can be removed by hydrogenation, dissolving the protected CBG in an organic solvent and reacting with hydrogen gas in the presence of a suitable catalyst, such as palladium on carbon. The process occur at a temperature of between −20° C. to 35° C. or any temperature within that range within +/−2, 5, 10, or 15° C. The resulting products include CBG.

EXAMPLES

Example Set 1

Table I, below, provides various example experiments for synthesizing CBG from olivetol and geraniol-derivatives. Column 1 indicates the entry, by number. Column 2 indicates the first reactant, column 3 indicates the third reactant, column 4 indicates a catalyst, column 5 indicates the solvent that was used, column 6 indicates the temperature at which the reactant-catalyst solution (or reactant solution) was held, column 7 indicates the amount of time that temperature was held, and column 8 indicates the percentage conversion of CBG (a percentage calculated by the amount of observed CBG (mols) divided by the starting amount of olivetol (mols) as measured using LC-MS analysis).

As indicated in Table I, various reactants, catalysts, solvents, and temperatures were used. It was observed that halogenated solvents may cause yields of CBG to increase.

TABLE I

| Entry | Reactant 1 | Reactant 2 | Catalyst | Solvent | Temperature | Times | % conversion |
|---|---|---|---|---|---|---|---|
| 1 | Olivetol | Geranyl bromide | Li2CO3 | Acetone | Room Temp | o/n | 0% |
| 2 | Olivetol | Geranyl bromide | Na2CO3 | Acetone | Room Temp | o/n | 15% |
| 3 | Olivetol | Geranyl bromide | K2CO3 | Acetone | Room Temp | o/n | 25% |
| 4 | Olivetol | Geranyl bromide | Cs2CO3 | Acetone | Room Temp | o/n | 15% |
| 5 | Olivetol | Geranyl bromide | Cs2CO3 | Acetonitrile | Room Temp | o/n | 25% |
| 6 | Olivetol | Geranyl bromide | K2CO3 | Acetone | 55 C. | 5 h | 0% |
| 7 | Olivetol | Geranyl bromide | K2CO3 | MTBE | Room Temp | o/n | 30% |
| 8 | Olivetol | Geranyl bromide | K2CO3, TBAI | Acetone | Room Temp | o/n | 0% |
| 9 | Olivetol | Geranyl bromide | TBAI | Toluene:30% KOH (1:1) | Reflux | 3 h | 0% |
| 10 | Olivetol | Geranyl bromide | TBAI | Acetone | 55 C. | 5 h | 0% |
| 11 | Olivetol | Geraniol | pTSA | MTBE | Room Temp | o/n | 0% |
| 12 | Olivetol | Geraniol | pTSA | Chloroform (10M) | Room Temp | o/n | 25% |
| 13 | Olivetol | Geraniol | pTSA | Chloroform (5M) | Room Temp | o/n | 25% |

TABLE I-continued

| Entry | Reactant 1 | Reactant 2 | Catalyst | Solvent | Temperature | Times | % conversion |
|---|---|---|---|---|---|---|---|
| 14 | Olivetol | Geraniol | pTSA | Chloroform (1M) | Room Temp | o/n | 30% |
| 15 | Olivetol | Geraniol | pTSA | Chloroform (0.25M) | Room Temp | o/n | 40% |
| 16 | Olivetol | Geraniol | pTSA | Chloroform (0.025M) | Room Temp | o/n | 40% |
| 17 | Olivetol | Geraniol | pTSA | None | 60 C. | 6 h | 20% |
| 18 | Olivetol | Geraniol | None | None | 60 C. | 6 h | 0% |
| 19 | Olivetol | Geranyl bromide | None | None | 60 C. | 6 h | 0% |
| 20 | Olivetol | Geraniol | BF3 | 1,4-Dioxane | Room Temp | 48 h | 10% |
| 21 | Olivetol | Geraniol | BF3, Al2O3 | CH2Cl2 | Room Temp | 10 s | 20% |
| 22 | Olivetol | Geraniol | BF3, SiO2 | CH2Cl2 | Room Temp | 48 h | 10% |
| 23 | Olivetol | Geranyl bromide | Montmorillonite | CH2Cl2 | Room Temp | 24 h | 0% |
| 24 | Olivetol | Geraniol | pTSA | CH2Cl2 | Room Temp | 24 h | 40% |
| 25 | Olivetol | Geraniol | pTSA, MgSO4 | CHCl3 | Room Temp | 24 h | 0% |
| 26 | Olivetol | Geranyl bromide | AgNO3 | Toluene | 55 C. | 24 h | 0% |
| 27 | Olivetol | Geraniol | pTSA | CHCl3 | 55 C. | 24 h | 0% |
| 28 | Olivetol | Geraniol | pTSA | CHCl3 | 55 C. | 5 h | 20% |

Example Set 2

Table II, below, provides various example experiments for synthesizing CBG from olivetol and geraniol. Column 1 indicates the entry, by number. Column 2 indicates the catalyst that was used, column 3 indicates the solvent, column 4 indicates the temperature at which the reactant-catalyst solution was held, column 5 indicates the amount of time that the temperature was held, column 6 indicates the conversion of CBG (a percentage calculated by the amount of observed CBG (mols) divided by the starting amount of olivetol (mols) as measured using LC-MS analysis), and column 8 indicates the percentage conversion of Compound B (a percentage calculated by the amount of observed Compound B (mols) divided by the starting amount of olivetol (mols) as measured using LC-MS analysis).

To perform the experiments indicated in table II, to a solution of olivetol (1 g, 5.5 mmol) and geraniol (0.96 mL, 5.5 mmol) in a solvent as indicated in Table II below, (5.5 mL) was added pTSA (10 mg). All reactions were analyzed by LC-MS.

Example 3

In a third example, to a suspension of olivetol (1.00 g, 5.55 mmol) in toluene (28 mL, 0.2 M) was added geraniol (1.50 g, 9.71 mmol) followed by pTSA (40 mg). The reaction was stirred at room temperature in the absence of light for 20 hours. The reaction was quenched with aq. sat. NaHCO₃ and the layers were separated. The organic layer was washed with brine, dried (MgSO₄), filtered, and concentrated in vacuo. The residue was purified by column chromatography (SiO₂, pet ether/ether) to afford cannabigerol (420 mg, 24% conversion), along with Compound B and Compound C. The products were characterized by H-NMR and LC-MS.

Example 4

In a fourth example, to a suspension of olivetol (1.00 g, 5.55 mmol) in chloroform (28 mL, 0.2 M) was added geraniol (1.50 g, 9.71 mmol) followed by pTSA (40 mg). The reaction was stirred at room temperature in the absence of light for 12 hours. The reaction was quenched with aq. sat.

TABLE II

| Entry | Catalyst | Solvent | Temperature | Time | % conversion CBG | Compound B |
|---|---|---|---|---|---|---|
| 1 | pTSA | CHCl3 | 55 C. | 5 h | 55% | 45% |
| 2 | pTSA | Acetonitrile | 50 C. | 5 h | 7% | 12% |
| 3 | pTSA | MTBE | 50 C. | 5 h | 25% | 25% |
| 4 | pTSA | Heptane | 50 C. | 5 h | 26% | 21% |
| 5 | pTSA | Toluene | 50 C. | 5 h | 55% | 36% |
| 6 | pTSA | Ethyl Acetate | 50 C. | 5 h | 25% | 25% |
| 7 | pTSA | Acetone | 50 C. | 5 h | 30% | 36% |
| 8 | pTSA | Ethanol | 50 C. | 5 h | 4% | 6% |
| 9 | pTSA | 1,4-Dioxane | 100 C. | 20 min | 36% | 44% |
| 10 | pTSA | t-Butyl Acetate | 100 C. | 20 min | 40% | 40% |
| 11 | pTSA | 2-Methyl THF | 100 C. | 20 min | 40% | 40% |
| 12 | pTSA | THF | 100 C. | 20 min | 36% | 44% |
| 11 | pTSA | Isobutyl acetate | 75 C. | 45 min | 40% | 40% |
| 12 | pTSA | Butyl acetate | 75 C. | 45 min | 40% | 40% |

NaHCO₃ and the layers were separated. The aqueous layer was extracted with chloroform and the combined organic extracts were washed with brine, dried (MgSO4), filtered, and concentrated in vacuo. The residue was purified by column chromatography (SiO2, pet ether/ether) to afford cannabigerol (420 mg, 24% conversion), Compound B (280 mg, 16% Conversion), and Compound C (712 mg, 28% Conversion). The products were characterized by 1H-NMR and LC-MS.

Example Set 5

Table III, below, provides various example experiments for synthesizing CBG from olivetol and geraniol. Column 1 indicates the entry, by number. Column 2 indicates the catalyst that was used, column 3 indicates the solvent, column 4 indicates the percentage conversion of CBG (a percentage calculated by the amount of observed CBG (mols) divided by the starting amount of olivetol (mols) as measured using LC-MS analysis), and column 5 indicates the percentage conversion of Compound B (a percentage calculated by the amount of observed CBG (mols) divided by the starting amount of olivetol (mols) as measured using LC-MS analysis).

For all experiments indicated by Table III, the following was performed: To a solution of olivetol (1 g, 5.5 mmol) and geraniol (0.96 mL, 5.5 mmol) in toluene (5.5 mL) was added the indicated catalyst (10 mg). The solution was stirred at 65° C. in the absence of light for 1 h. The reactions were quenched by addition of solid NaHCO₃, dried (MgSO4), filtered and concentrated in vacuo. All crude reactions were analyzed by LC-MS.

TABLE III

| Entry | Catalyst | Solvent | % conversion CBG | Compound B |
|---|---|---|---|---|
| 1 | pTSA | Toluene | 55% | 36% |
| 2 | CSA | Toluene | 54% | 36% |
| 3 | TFA | Toluene | <6% | <4% |
| 4 | AcOH | Toluene | <6% | <4% |
| 5 | Formic acid | Toluene | <12% | <10% |
| 6 | BF3 | Toluene | 25% | 25% |
| 7 | ZnBr2 | Toluene | <5% | <5% |
| 8 | MsOH | Toluene | 40% | 30% |
| 9 | FeCl3 | Toluene | 25% | 25% |
| 10 | AcCl | Toluene | 25% | 25% |

Example Set 6

Table IV, below, provides various example experiments for synthesizing CBG from olivetol and geraniol. Column 1 indicates the entry, by number. Column 2 indicates the catalyst that was used, column 3 indicates the temperature of the reaction, column 4 indicates the residence time of the reaction, column 5 indicates the conversion of CBG (a percentage calculated by the amount of observed CBG (mols) divided by the starting amount of olivetol (mols) as measured using LC-MS analysis), and column 5 indicates the conversion of Compound B (a percentage calculated by the amount of observed CBG (mols) divided by the starting amount of olivetol (mols) as measured using LC-MS analysis). All reactions indicated in Table IV were run in toluene (1 M) with 1% catalyst loading.

TABLE IV

| Entry | Catalyst | Temperature | Time | % conversion CBG | Compound B |
|---|---|---|---|---|---|
| 1 | pTSA | negative 10 C. | 24 h | 26% | 14% |
| 2 | pTSA | 0 C. | 24 h | 51% | 27% |
| 3 | pTSA | 20 C. | 24 h | 48% | 35% |
| 4 | pTSA | 35 C. | 18 h | 28% | 23% |
| 5 | pTSA | 55 C. | 1.5 h | 47% | 34% |
| 6 | pTSA | 65 C. | 1 h | 55% | 45% |
| 7 | pTSA | 75 C. | 40 min | 55% | 45% |
| 8 | pTSA | 100 C. | 20 min | 55% | 45% |

Example Set 7

Table V, below, provides various example experiments for synthesizing CBG from olivetol and geraniol. Column 1 indicates the entry, by number. Column 2 indicates the catalyst that was used, column 3 indicates the temperature of the reaction, column 4 indicates the catalyst loading percentage as defined by % weight relative to olivetol, column 5 indicates molar concentration of the olivetol, column 6 indicates the residence time of the reaction, column 7 indicates a percentage conversion of CBG (a percentage calculated by the amount of observed CBG (mols) divided by the starting amount of olivetol (mols) as measured using LC-MS analysis), and column 8 indicates the percentage conversion of Compound B (a percentage calculated by the amount of observed Compound B (mols) divided by the starting amount of olivetol (mols) as measured using LC-MS analysis). All reactions indicated in Table V were run in toluene.

TABLE V

| Entry | Catalyst | Temperature | Catalyst Loading | Concentration | Time | % conversion | Compound B |
|---|---|---|---|---|---|---|---|
| 1 | pTSA | 55 C. | 1% | 1M | 5 h | 47% | 34% |
| 2 | pTSA | 65 C. | 1% | 2M | 1 h | 53% | 47% |
| 3 | pTSA | 75 C. | 1% | 5M | 20 min | 54% | 46% |
| 4 | pTSA | 0 C. | 10% | 0.02M | 24 h | 52% | 28% |
| 5 | pTSA | 0 C. | 10% | 0.2M | 24 h | 55% | 29% |
| 6 | pTSA | 0 C. | 10% | 1M | 24 h | 51% | 27% |
| 7 | pTSA | 0 C. | 10% | 2M | 24 h | 44% | 36% |
| 8 | pTSA | 0 C. | 10% | 5M | 24 h | 44% | 36% |
| 9 | pTSA | 0 C. | 10% | 10M | 24 h | 38% | 47% |

Example Set 8

Table VI, below, provides various example experiments for synthesizing CBG from olivetol and geraniol. Column 1 indicates the entry, by number. Column 2 indicates the catalyst that was used, column 3 indicates the temperature of the reaction, column 4 indicates the catalyst loading percentage catalyst loading percentage as defined by % weight relative to olivetol, column 5 indicates the residence time of the reaction, column 6 indicates a percentage conversion of CBG (a percentage calculated by the amount of observed Compound B (mols) divided by the starting amount of olivetol (mols) as measured using LC-MS analysis), and column 7 indicates the percentage conversion of Compound B (a percentage calculated by the amount of observed Compound B (mols) divided by the starting amount of olivetol (mols) as measured using LC-MS analysis). All reactions indicated in Table V were run in toluene.

TABLE VI

| Entry | Catalyst | Temperature | Catalyst Loading | Time | % conversion | Compound B |
|---|---|---|---|---|---|---|
| 1 | pTSA | 55 C. | 1% | 5 h | 48% | 32% |
| 2 | pTSA | 75 C. | 0.50% | 20 min | 49% | 40% |
| 3 | pTSA | 0 C. | 1% | 24 h | 19% | 10% |
| 4 | pTSA | 0 C. | 2% | 24 h | 26% | 14% |
| 5 | pTSA | 0 C. | 3% | 24 h | 31% | 21% |
| 6 | pTSA | 0 C. | 4% | 24 h | 34% | 27% |

Example 9

In a ninth example, to a solution of olivetol (3 g, 16.5 mmol) and geraniol (2.9 mL, 16.5 mmol) in toluene (8.2 mL, 2 M) was added pTSA (30 mg, 1 wt. %). The reaction was heated to 75° C. and stirred at temperature for 45 mins. in the absence of light. The reaction was then cooled to room temperature and solid NaHCO$_3$ was added. The mixture was filtered through a pad of MgSO$_4$, washed with heptane and concentrated in vacuo. The residue was taken up in heptane (6 mL) and stored at −20° C. overnight. No precipitation was observed, so the solution was warmed and filtered through a plug of silica. The silica was washed with heptane (10 mL) and a 5% EtOAc in heptane solution (10 mL). The combined washes and filtrate were concentrated in vacuo, dissolved in heptane (3 mL) and stored at −20° C. overnight. The precipitant was filtered, washed with heptane, and recrystallized from heptane to afford cannabigerol (486 mg, 9% conversion) as a white solid. The remaining mother liquor contains CBG that may be purified by column chromatography (SiO$_2$, pet ether/ether) to recover additional product.

Example 10

In a tenth example, Olivetol (500 g, 2.8 mol) and toluene (6 kg) were added to a 50 L reactor, followed by geraniol (750 g, 4.8 mol) and toluene (6 kg) sequentially. The mixture was stirred (350 rpm) and cooled to 10° C. After 1 h, the internal temperature reached 10° C., and pTSA (15 g) was added. The reaction was stirred at 10° C., in the absence of light for 72 h. At this time the reaction was deemed 50% complete by HPLC analysis. The reaction was quenched with NaHCO$_3$ (5 g), and stirred for 15 min. At this time, the reaction was filtered through a plug of silica (500 g), and concentrated in vacuo to yield 1093 g of residue. The residue was distilled in a wiped film evaporator with internal core temperature of 70° C. and outer wall temperature of 140° C., with a vacuum between 200 and 300 mtorr. The fraction with the highest boiling point (residue side) was collected (471 g) and taken up in petroleum ether (3:1 pet ether:residue, volume:mass) and stored at −20° C. for 40 hours. The precipitate (159 g) was filtered, taken up in warm heptane (10:1), and stored at 20° C. for 16 hours. The crystals (76 g) were filtered and dried. The remaining mother liquor was stored at 5° C. for 16 hours. The crystals (39 g) were filtered and dried. The combined yields afforded CBG (115 g, 13% yield) in high purity, without the need for chromatography. The combined mother liquors contained additional CBG that can be purified by chromatography to increase yields.

Example 11

In an eleventh example, to a solution of olivetol (10 g, 55 mmol) and geraniol (9.6 mL, 55 mmol) in toluene (11 mL, 5 M) was added para-toluenesulfonic acid (50 mg). The reaction was heated to 75° C. and stirred at that temperature for 20 min. At this time the reaction was cooled to room temperature. Solid NaHCO$_3$ (50 mg) and MgSO$_4$ (7 g) were added and the mixture was filtered and washed with heptane (3×100 mL). The solvent was removed in vacuo and the residue was taken up in heptane (1:1) and filtered through a plug of silica (60 g) with a 5% tert-butylmethyl ether in heptane (600 mL). The solvent was removed in vacuo and the residue was taken up in heptane (2:1) and stored at −20° C. for 12 h. The precipitated CBG was filtered and washed with cold heptane (3×30 mL) to afford CBG at 91% purity. The solid CBG was taken up in warm heptane (2:1) and stored at room temperature for 16 h. The resulting crystals were filtered and washed with cold heptane (3×3 mL) to afford CBG crystals of >98% purity.

Example 12

In a twelfth example, to a solution of olivetol (1 g, 5.5 mmol) and geraniol (0.96 mL, 5.5 mmol) in toluene (5.5 mL, 1 M) was added para-toluenesulfonic acid (10 mg). The reaction was heated to 75° C. and stirred at that temperature for 45 min. At this time the reaction was cooled to room temperature. Solid NaHCO$_3$ (10 mg) and MgSO$_4$ (700 mg) were added and the mixture was filtered and washed with heptane (3×10 mL). The solvent was removed in vacuo and the residue was taken up in heptane (2:1) and stored at −20° C. for 12 h. The precipitated CBG was filtered and washed with cold heptane (3×3 mL) to afford CBG at 94% purity. The solid CBG was taken up in warm heptane (2:1) and stored at room temperature for 16 h. The resulting crystals were filtered and washed with cold heptane (3×3 mL) to afford CBG crystals of >98% purity.

Example 13

Table VII below, provides various example experiments for synthesizing CBG from olivetol and geraniol in the absence of a solvent. Column 1 indicates the entry, by number. Column 2 indicates the catalyst that was used, if any, column 3 indicates the temperature of the reaction, column 4 indicates the catalyst loading percentage as defined by % weight relative to olivetol, column 5 indicates the residence time of the reaction, column 6 indicates a percentage conversion of CBG (a percentage calculated by the amount of observed Compound B (mols) divided by the starting amount of olivetol (mols) as measured using LC-MS analysis), and column 7 indicates the percentage conversion of Compound B (a percentage calculated by the amount of observed Compound B (mols) divided by the starting amount of olivetol (mols) as measured using LC-MS analysis).

TABLE VII

| Entry | Reagent | Temperature | Catalyst Loading | Time | % conversion | Compound B |
|---|---|---|---|---|---|---|
| 1 | pTSA | 0 C. | 10% | 24 h | 34% | 51% |
| 2 | n/a | 170 C. | n/a | 24 | 13.1%* | Not measured |
| 3 | n/a | 150 C. | n/a | 24 h | 13%* | Not measured |
| 4 | n/a | 80 C. | n/a | 24 h | 0% | Not measured |
| 5 | MgSO4 | 85 C. | n/a | 24 h | 6% | Not measured |
| 6 | MgSO4 | 55 C. | n/a | 24 h | 4% | Not measured |
| 7(a) | n/a | 120 C. | n/a | 30 h | 26% | Not measured |
| 7(b) | n/a | 135 C. | n/a | 7(a) + 30 h | 54% | Not measured |

Example Set 14 (2-iodo-olivetol with prenyl bromide)

Table VIII indicates the experimental results of the following reaction:

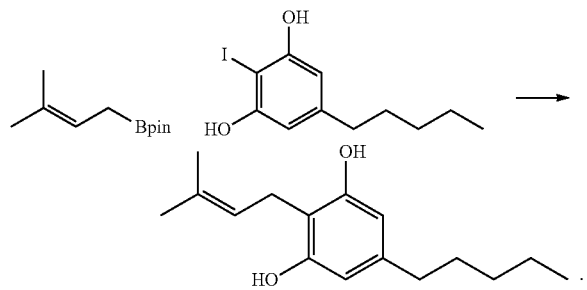

The column headings 1, 2, 3, 4, 5, and 6 represent the catalyst that was used, where 1 indicates XPhos-Pd-G3, 2 indicates SPhos-Pd-G2, 3 indicates cataCXium-A-Pd-G3, 4 indicates APhos-Pd-G3, 5 indicates P(Cy)3-Pd-G3, and 6 indicates PEPPSI-IPENT. The row headings indicate the solvent that was used, where A indicates DMA, B indicates toluene, C indicates n-butanol, and D indicates THF. The interior of the table indicates the result of using the indicated catalyst with the solvent. A P indicates the Formula VI was detected by LCMS, a T indicates trace amounts of Formula VI were detected by LCMS, and an X indicates that Formula VI was not detected.

Table VIII was populated using the following method: To each of four 1 dram vials, was added 22 mg 2-iodo-5-pentyl-1,3-benzenediol. The vials were labeled A, B, C, and D fitted with stir bars, and then placed in a nitrogen-purged inert box. To each vial was then added 675 µL of degassed solvent, with N,N-dimethylacetamide, toluene, 1-butanol, and tetrahydrofuran added to vials A, B, C, and D respectively. With stirring, 26 L of 4,4,5,5-Tetramethyl-2-(3 methyl-2-buten-1-yl)-1,3,2-dioxaborolane was added to each reagent mixture. A 4×6 array (rows A-D by columns 1-6) of vials pre-loaded with palladium catalysts and stir bars was loaded into an aluminum reaction block in the inert box. Columns 1-6 contained the following catalysts: XPhos-Pd-G3, SPhos-Pd-G2, cataCXium-A-Pd-G3, APhos-Pd-G3, P(Cy)$_3$-Pd-G3, and PEPPSI-IPent respectively. To each row of vials in the array, 100 µL of reagent mixture was added, resulting in a screen of the 24 available solvent-catalyst combinations. The aluminum reaction block was sealed in the inert box, and then transferred to a stirring hot-plate at 60° C. After stirring for 18 h the reaction block was cooled to room temperature, and the reactions were quenched by addition of 500 µL of 2% acetic acid in acetonitrile to each vial. The vials were stirred at room temperature for at least 3 min prior to further dilution and analysis. From each vial 25 µL of solution was diluted into 700 µL of acetonitrile, and the subsequent mixtures were analyzed by LCMS for product formation.

TABLE VIII

|   | 1 | 2 | 3 | 4 | 5 | 6 |
|---|---|---|---|---|---|---|
| A | T | T | T | T | T | T |
| B | T | T | T | X | T | T |
| C | P | P | P | P | P | D |
| D | T | T | T | T | T | T |

Example Set 15 (bis(methoxy)-2-iodo-olivetol with prenyl bromide)

Table IX indicates the experimental results of the following reaction:

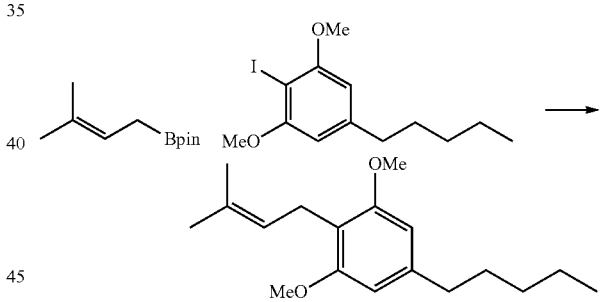

The column headings 1, 2, 3, 4, 5, and 6 represent the catalyst that was used, where 1 indicates XPhos-Pd-G3, 2 indicates SPhos-Pd-G2, 3 indicates cataCXium-A-Pd-G3, 4 indicates APhos-Pd-G3, 5 indicates P(Cy)3-Pd-G3, and 6 indicates PEPPSI-IPENT. The row headings indicate the solvent that was used, where A indicates DMA, B indicates toluene, C indicates n-butanol, and D indicates THF. The interior of the table indicates the result of using the indicated catalyst with the solvent. A P indicates the Formula VI was detected by LCMS, a T indicates trace amounts of Formula VI were detected by LCMS, and an X indicates that Formula VI was not detected.

Table IX was populated using the following method: To each of four 1 dram vials, was added 24 mg 2-iodo-1,3-dimethoxy-5-pentylbenzene. The vials were labeled A, B, C, and D fitted with stir bars, and then placed in a nitrogen-purged inert box. To each vial was then added 673 µL of degassed solvent, with N,N-dimethylacetamide, toluene, 1-butanol, and tetrahydrofuran added to vials A, B, C, and D respectively. With stirring, 26 µL of 4,4,5,5-Tetramethyl-2-

(3-methyl-2-buten-1-yl)-1,3,2-dioxaborolane was added to each reagent mixture. A 4×6 array (rows A-D by columns 1-6) of vials pre-loaded with palladium catalysts and stir bars was loaded into an aluminum reaction block in the inert box. Columns 1-6 contained the following catalysts: XPhos-Pd-G3, SPhos-Pd-G2, cataCXium-A-Pd-G3, APhos-Pd-G3, P(Cy)3-Pd-G3, and PEPPSI-IPent respectively. To each row of vials in the array, 100 μL of reagent mixture was added, resulting in a screen of the 24 available solvent-catalyst combinations. The aluminum reaction block was sealed in the inert box, and then transferred to a stirring hot-plate at 60° C. After stirring for 18 h the reaction block was cooled to room temperature, and the reactions were quenched by addition of 500 μL of 2% acetic acid in acetonitrile to each vial. The vials were stirred at room temperature for at least 3 min prior to further dilution and analysis. From each vial 25 μL of solution was diluted into 700 μL of acetonitrile, and the subsequent mixtures were analyzed by LCMS for product formation.

TABLE IX

|   | 1 | 2 | 3 | 4 | 5 | 6 |
|---|---|---|---|---|---|---|
| A | P | P | P | P | P | X |
| B | P | P | P | P | P | X |
| C | P | P | P | P | P | X |
| D | T | T | T | P | T | X |

Example 16 (Reactions of Geranyl Bpin to Variously Protected 2-iodo-olivetols)

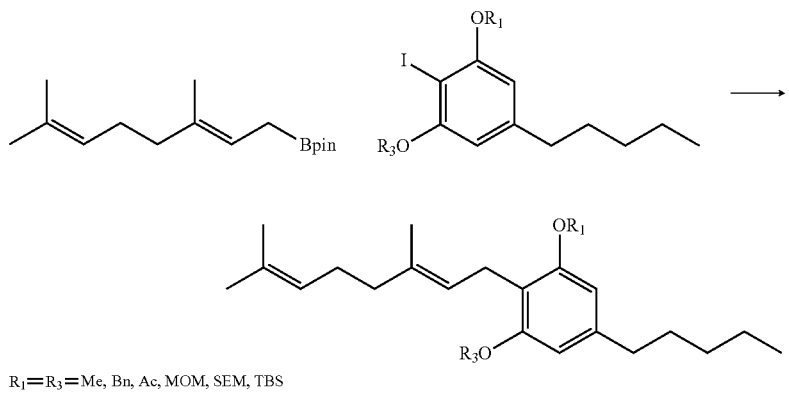

$R_1=R_3=$Me, Bn, Ac, MOM, SEM, TBS

In a sixteenth example, to each of six 1 dram vials, was added either 2-iodo-1,3-bis(methoxy)-olivetol (20 mg, 0.06 mmol), 2-iodo-1,3-bis(benzyl)-olivetol (29 mg, 0.06 mmol), 2-iodo-1,3-bis(acetoxy)-olivetol (23 mg, 0.06 mmol), 2-iodo-1,3-bis(methoxymethyl ether)-olivetol (24 mg, 0.06 mmol), 2-iodo-1,3-bis[2-(trimethylsiloxy)methoxyethyl]-olivetol (34 mg, 0.06 mmol), or 2-iodo-1,3-bis(t-butyldimethylsilyl)-olivetol (32 mg, 0.06 mmol). The vials were labeled A, B, C, D, E, and F, fitted with stir bars, and then placed in a nitrogen-purged inert box. To each vial was then added 600 μL of degassed 1-butanol. With stirring, 24 mg of geranyl Bpin was added to each reagent mixture. Six vials pre-loaded with SPhos-Pd-G2 (4.3 mg), KPO$_4$ (1.5 M in H$_2$O, 120 μL) and stir bars were loaded into an aluminum reaction block in the inert box. To each row of vials in the array, 100 μL of each respective reagent mixture was added. The aluminum reaction block was sealed ii the inert box, and then transferred to a stirring hot-plate at 60° C. After stirring for 18 h the reaction block was cooled to room temperature, and the reactions were quenched by addition of 500 μL of 2% acetic acid in acetonitrile to each vial. The vials were stirred at room temperature for at least 3 min prior to further dilution and analysis. From each vial 25 μL of solution was diluted into 700 μL of acetonitrile, and the subsequent mixtures were analyzed by LCMS for product formation. No product detected by LCMS for the benzyl, SEM, or TBS. Product detected by LCMS for acetoxy, MOM and methoxy. $^1$H-NMR confirmed 78% yield of methoxy, 86% yield of MOM, and was inconclusive for acetoxy.

Example 17 (gernayl Bpin coupled with bis(methoxy)-2-iodo-olivetol)

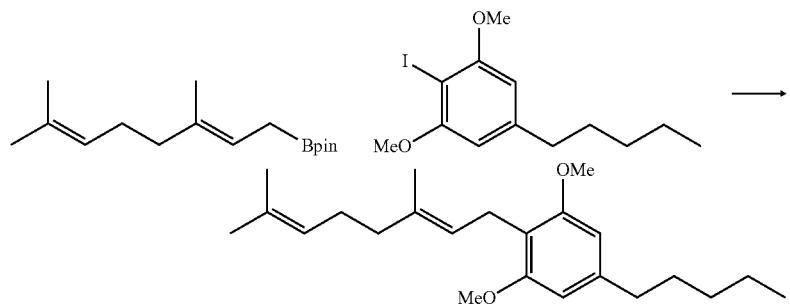

In a seventeenth example, to a 1 dram vial, was added 2-iodo-1,3-bis(methoxy)-olivetol (20 mg, 0.06 mmol). The vial was fitted with a stir bar, and then placed in a nitrogen-purged inert box. To the vial was added degassed 1-butanol (600 µL, 0.1 M). With stirring, geranyl Bpin (24 mg, 0.091 mmol) was added to the reagent mixture. The mixture was added to a vial containing SPhos-Pd-G2 (4.3 rig) and K3PO4 (1.5 M in H2O, 120 µL). The reaction was sealed in the inert box, and then transferred to a stirring hot-plate at 60° C., After stirring for 18 h the reaction block was cooled to room temperature, and the reactions were quenched by addition of 500 µL of 2%0 acetic acid in acetonitrile to each vial. The vials were stirred at room temperature for at least 3 min prior to further dilution and analysis. From each vial 25 µL of solution was diluted into 700 µL of acetonitrile, and the subsequent mixtures were analyzed by LCMS for product formation. LCMS analysis confirmed the desired product, 1,3-bis(methoxy)-cannabigerol, was formed as the major product. 1H-NMR showed an 85% yield of product.

Example 18 (Reaction of bis(methoxy)-2-Bpin-olivetols to Geranyl Bromide in Various Solvents)

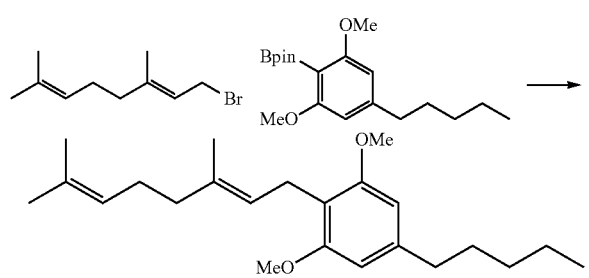

In an eighteenth example, to each of four 1 dram vials, was added 2-Bpin-1,3-bis(methoxy)-olivetol (30 rug, 0.09 mmol). The vials were labeled A, B, C, and D fitted with stir bars, and then placed in a nitrogen-purged inert box. To each vial was then added 600 µL of degassed solvent, with N,N-dimethylacetamide, toluene, 1-butanol, and tetrahydrofuran added to vials A, B. C, and D respectively. With stirring, 12 µL of geranyl bromide was added to each reagent mixture. To four vials pre-loaded with XPhos-Pd-G3 (5.1 mg) was added each reagent mixture. The aluminum reaction block was sealed in the inert box, and then transferred to a stirring hot-plate at 60° C. After stirring for 18 h the reaction block was cooled to room temperature, and the reactions were quenched by addition of 500 µL of 2% acetic acid in acetonitrile to each vial. The vials were stirred at room temperature for at least 3 min prior to further dilution and analysis. From each vial 25 µL of solution was diluted into 700 µL of acetonitrile, and the subsequent mixtures were analyzed by LCMS for product formation. 1H-NMR confirmed product in the N,N-dimethylacetamide N-dimeth lacetamide reaction and showed 19% yield in toluene, 25% yield in butanol, and 24% yield in THF.

Example 19 (Reactions of Various 2-Bpin-olivetols to Geranyl Bromide in Butanol)

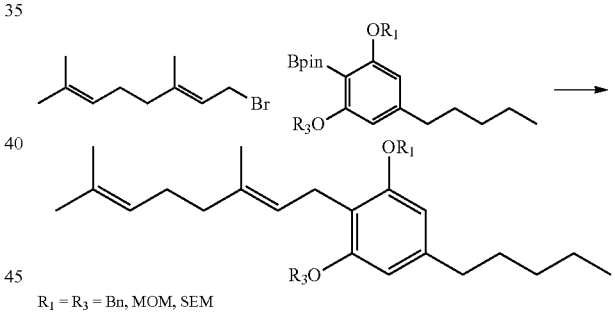

$R_1 = R_3 = $ Bn, MOM, SEM

In an nineteenth example, to each of three 1 dram vials, was added either 2-Bpin-1,3-bis(benzyl)-olivetol (44 mg, 0.09 mmol), 2-Bpin-1,3-bis(methoxymethyl ether)-olivetol (35 mg, 0.09 mmol), or 2-Bpin-1,3-bis[2-(trimethylsiloxy)methoxyethyl]-olivetol (51 mg, 0.09 mmol). The vials were labeled A, B, and C, fitted with stir bars, and then placed in a nitrogen-purged inert box. To each vial was then added 600 µL of degassed 1-butanol. With stirring, 12 µL of geranyl bromide was added to each reagent mixture. Three vials were loaded with XPhos-Pd-G3 (5.1 mg), K3PO4 (1.5 M in H₂O, 120 µL) and stir bars, and the vials were loaded into an aluminum reaction block in the inert box. The aluminum reaction block was sealed in the inert box, and then transferred to a stirring hot-plate at 60° C. After stirring for 18 h the reaction block was cooled to room temperature, and the reactions were quenched by addition of 500 µL of 2% acetic acid in acetonitrile to each vial. The vials were stirred at room temperature for at least 3 min prior to further dilution and analysis. From each vial 25 µL of solution was diluted into 700 μL of acetonitrile, and the subsequent mixtures were analyzed by LCMS for product formation. LCMS analysis confirmed product in the MOM and SEM reactions. No product was detected in the benzyl reaction.

Example 20 (2-iodo-1,3-bis(methoxymethyl ether)-olivetol prep)

In a twentieth example, 2-iodo-olivetol (500 mg, 1.633 mmol) and tetrabutylammonium iodide (60 mg, 0.163 mmol) were charged into a 20 mL vial with a stir bar. The solids were dissolved in methylene chloride (2.6 mL), the vial sealed with a PTFE screw top septum, and the vessel placed in an ice bath. A solution of MOM chloride (6.5 M in methyl acetate, 0.75 mL) was added in one portion via syringe. DIPEA (654 mg, 5.064 mmol) was added dropwise via syringe with rapid stirring and the solution allowed to warm to rt following completion of the addition. Reaction progress was monitored by TLC (1:4 diethyl ether-pet ether, UV and 12). After 2.5 hours the reaction was concentrated under a stream of nitrogen, saturated aqueous ammonium chloride added (4 mL), and the mixture stirred for 30 minutes. The aqueous was extracted with diethyl ether-petroleum ether (1:4, 3×5 mL), the combined organics washed with brine, and dried over magnesium sulphate. The solution was filtered and concentrated to give an orange oil. The oil was purified with a Biotage system (diethyl ether-pet ether gradient) to give a colorless oil.

Example 21 (2-Bpin-1,3-bis(methoxymethyl ether)-olivetol prep)

In a twenty-first example, magnesium turnings (16 mg, 0.660 mmol) and iodine (6.4 mg, 0.025 mmol) were charged into a hot 1 dram with a stir bar vial and cooled under a stream of nitrogen. The solids were suspended in THF (100 μL) to give an orange-brown suspension. Pinacol borane (97 mg, 0.760 mmol) was added via syringe. 2-iodo-1,3-bis (methoxymethyl ether)-olivetol (200 mg, 0.507 mmol) as a solution in TH-IF (500 μL) was added dropwise via syringe The vial was heated to 60° C. and stirred overnight. The reaction was cooled to rt, diluted with petroleum ether, quenched with 0.1 N HCl (500 μL), and stirred for 15 min. The organic layer was separated and the aqueous layer was extracted with petroleum ether (3×2 mL). The combined organic layers were dried (MgSO4), filtered, and concentrated in vacuo to give a light yellow oil.

Example 22 (2-boronic acid-1,3-bis(methoxymethyl ether)-olivetol prep)

In a twenty second example, 1,3-bis(methoxymethyl ether)-olivetol (100 mg, 0.373 mmol, 1 eq) was charged into an oven dried 1 dram vial with stir bar, the vial purged with nitrogen, and sealed with a screw top PTFE septum. Anhydrous THF was added via syringe and the solution cooled to 0° C. in an ice bath. A solution of n-butyllithium (1.6 Min hexane, 280 μL, 1.2 eq) was added dropwise via syringe with rapid stirring. The yellow solution was maintained at 0° C. for 1 hour. Trimethylborate (116 mg, 1.119 mmol, 3 eq) was added dropwise at 0° C. During the course of the addition the reaction became hazy grey, and the mixture was allowed to warm to rt overnight. The reaction was quenched with water (500 μL) and stirred for 30 minutes. The solution was acidified with dilute aqueous hydrochloric acid, which caused the formation of a foamy white precipitate. The precipitate was dissolved in ethyl acetate, the organic layer decanted, and the aqueous extracted with ethyl acetate (2×4 mL). The combined organics were dried over magnesium sulphate, filtered, and concentrated to give an amorphous white solid (103 mg). The material was used without further purification.

Example 23 (2-boronic acid-1,3-bis(methoxymethyl ether)-olivetol and Geraniol Coupling)

In a twenty-third example, to an oven dried 1 dram vial with stir bar was added 2-boronic acid-1,3-bis(methoxymethyl ether)-olivetol (19 mg, 0.060 mmol, 1 eq) and palladium-tetrakis(triphenylphophine) (7 mg, 0.006 mmol, 0.1 eq). The vial was purged with nitrogen and sealed with a screw top PTFE septum. Geraniol (14 mg, 0.090 mmol, 1.5 eq) was added in portion via syringe as a solution in anhydrous TH-IF (600 μL) to give a homogenous yellow solution. The vial was placed in a vial block preheated to 80° C., and rapidly agitated for 17 hours, at which point the reaction was light orange and a black precipitate had formed. The reaction was diluted with diethyl ether and petroleum ether (1:1, 3 mL total), and the suspension filtered through a Celite pad. The mixture was concentrated to give a light orange oil (22.8 mg). TLC analysis (1:4 diethyl ether-pet ether, KMnO4) indicated some formation of product. Semi-quantitative NMR analysis (CDCl3, nitromethane standard) indicated 16% purity of 1,3-bis(methoxymethyl ether)-cannabigerol in the unpurified mixture. LC-MS trace also showed an unquantified amount of target compound.

Example 24 (1,3-bis(methoxymethyl ether)-cannabigerol Deprotection to CBG)

In a twenty fourth example, 1,3-bis(methoxymethyl ether)-cannabigerol (20 mg, 0.035 mmol, 1 eq) was charged into a 1 dram vial and dissolved in methanol (350 μL) and diethyl ether (50 μL). Methanesulfonic acid (0.4 mg, 0.004 mmol, 0.1 eq) was added, the vial capped, and placed into a 4° C. refrigerator. Reaction progress was monitored by TLC (1:4 diethyl ether-petroleum ether, KMnO4) and LC-MS until full consumption of starting material and partially deprotected intermediates.

Example 25 (1,3-bis[2-(trimethylsiloxy)methoxyethyl]-cannabigerol Deprotection to CBG))

In a twenty-fifth example, 1,3-bis[2-(trimethylsiloxy) methoxyethyl]-cannabigerol (20 mg, 0.035 mmol, 1 eq) was charged into a 1 dram vial and dissolved in methanol (350 μL) and diethyl ether (50 μL). Methanesulfonic acid (0.4 mg, 0.004 mmol, 0.1 eq) was added, the vial capped, and placed into a 4° C. refrigerator. Reaction progress was monitored by TLC (1:4 diethyl ether-petroleum ether, KMnO4) and LC-MS until full consumption of starting material and partially deprotected intermediates.

Example 26 (1,3-bis[2-(trimethylsiloxy)methoxyethyl]-cannabigerol deprotection to 1-[2-(trimethylsiloxy)methoxyethyl]-cannabigerol)

In a twenty-sixth 1,3-bis[2-(trimethylsiloxy)methoxyethyl]-cannabigerol (20 mg, 0.035 mmol, 1 eq) was charged into a 1 dram vial with a stir bar, dissolved in dry THF (350 μL), and the vial sealed with a PTFE screw top septum. The reaction was cooled to 0° C. in an ice bath and tetrabutylammonium fluoride (1 M in THF, 0.105 mmol, 3 eq) was added dropwise via syringe. The reaction was allowed to warm to rt overnight. Reaction progress was monitored by TLC (1:4 diethyl ether-petroleum ether, KMnO4). After 25 hours the reaction was warmed to 60° C. in a preheated vial block and allowed to stir overnight. The reaction was a neon-salmon color and TLC analysis indicated complete conversion to the mono-deprotection product.

What is claimed:

1. A method comprising:
providing a first compound having the structure

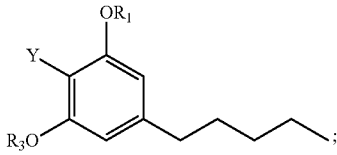

combining the first compound with a second compound having the structure:

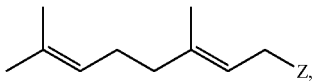

in a solvent to form a solution;
adding a suitable cross coupling metal catalyst to the solution to form an active mixture; and
reacting the active mixture to form a reacting mixture, wherein the reacting mixture contains a detectable amount of a third compound having the structure:

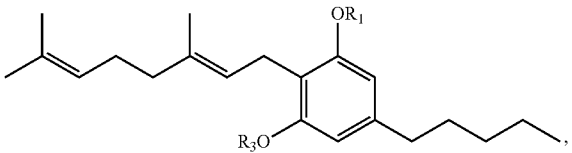

wherein $R_1$ and $R_3$ each are selected from the group consisting of: SEM, MOM, Me, Bn, TBS, and hydrogen;
wherein Z is selected from the group consisting of: boronate group, boronic acid, iodide, and bromide; and
wherein Y is selected from the group consisting of: iodide, bromide, a boronate group, and boronic acid group.

2. The method of claim 1, wherein the solvent is selected from the group consisting of: N,N-dimethylacetamide, toluene, 1-butanol, tetrahydrofuran, and mixtures thereof.

3. The method of claim 1, wherein the catalyst is selected from the group consisting of: XPhos-Pd-G3 ((2-Dicyclohexylphosphino-2',4',6'-triisopropyl-1,1'-biphenyl)[2-(2'-amino-1,1'-biphenyl)]palladium(II) methanesulfonate); SPhos-Pd-G2 (Chloro(2-dicyclohexylphosphino-2',6'-dimethoxy-1,1'-biphenyl)[2-(2'-amino-1,1'-biphenyl)]palladium (II)); cataCXium-A-Pd-G3 (Mesylate[(di(1-adamantyl)-n-butylphosphine)-2-(2'-amino-1,1'-biphenyl)]palladium(II)); APhos-Pd-G3 ([4-(Di-tert-butylphosphino)-N,N-dimethylaniline-2-(2'-aminobiphenyl)]palladium(II) methanesulfonate); P(Cy)3-Pd-G3 ([(Tricyclohexylphosphine)-2-(2'-aminobiphenyl)]palladium(II) methanesulfonate); PEPPSI-IPent (Dichloro[1,3-bis(2,6-Di-3-pentylphenyl) imidazol-2-ylidene](3-chloropyridyl)palladium(II)); and Pd(PPh3)4 (Palladium-tetrakis(triphenylphosphine)).

4. The method of claim 1, wherein Y is pinacol boronate.

* * * * *